United States Patent
Mockett et al.

(10) Patent No.: US 9,649,324 B2
(45) Date of Patent: May 16, 2017

(54) USE OF TYLVALOSIN AS ANTIVIRAL AGENT

(71) Applicants: ECO ANIMAL HEALTH LIMITED, New Malden (GB); CAMBRIDGE UNIVERSITY TECHNICAL SERVICES, Cambridge (GB)

(72) Inventors: Albert Philip Adrian Mockett, New Malden (GB); Thomas David Kay Brown, Cambridge (GB); Amanda Denise Stuart, Cambridge (GB)

(73) Assignees: ECO ANIMAL HEALTH LIMITED, New Malden (GB); CAMBRIDGE UNIVERSITY TECHNICAL SERVICES, Cambridge (GB)

( * ) Notice: Subject to any disclaimer, the term of this patent is extended or adjusted under 35 U.S.C. 154(b) by 0 days.

(21) Appl. No.: 14/733,801

(22) Filed: Jun. 8, 2015

(65) Prior Publication Data
US 2015/0313929 A1 Nov. 5, 2015

Related U.S. Application Data

(62) Division of application No. 12/373,657, filed as application No. PCT/GB2007/002620 on Jul. 13, 2006, now Pat. No. 9,066,964.

(30) Foreign Application Priority Data

Jul. 13, 2006 (GB) .................................. 0613952.1
Nov. 1, 2006 (GB) .................................. 0621782.2

(51) Int. Cl.
*A61K 31/35* (2006.01)
*A61K 31/7048* (2006.01)

(52) U.S. Cl.
CPC ............................. *A61K 31/7048* (2013.01)

(58) Field of Classification Search
CPC ........ A61K 31/7048; A23K 1/84; A61P 31/32
See application file for complete search history.

(56) References Cited

U.S. PATENT DOCUMENTS

| 1,978,409 A | 10/1934 | Carlson |
| 4,092,473 A | 5/1978 | Okamoto et al. |
| 2004/0082524 A1 | 4/2004 | Sanders |

FOREIGN PATENT DOCUMENTS

| JP | 2004-511498 A | 4/2004 |
| WO | WO-0232233 A2 | 4/2002 |
| WO | WO-2005002593 A1 | 1/2005 |

OTHER PUBLICATIONS

Adachi et al., Inhibition of betanodavirus infection by inhibitors of endosomal acidification. Arch Virol. 2007; 152(12) Abstract.
Helenius et al. On the entry of semliki forest virus into BHK-21 cells. J. Cell Biology. 1980; 84:404-20.
Wolff et al. (Burger's Medicinal Chemistry, 5th Ed., vol. 1, pp. 975-977, 1994).
Testa, Bernard, Biochemical Pharmacology, Prodrug Research: futile or fertile? 68 (2004) 2097-2106.
Thacker et at (Vaccine vol. 18, 2000, pp. 1244-1252.
Kobayashi et al., abstract only, J. Vet. Me. Sci. 1996, vol. 58 (2), pp. 109-13.
Kreutz et al., Virus research, vol. 42, 1996 pp. 137-147.

*Primary Examiner* — Savitha Rao
(74) *Attorney, Agent, or Firm* — Venable LLP; Keith G. Haddaway

(57) ABSTRACT

The Invention relates to the use of antibiotic, tylvalosin, as an anti-viral agent. Tylvalosin is particularly useful for the treatment of PRRSV.

6 Claims, 15 Drawing Sheets

USE OF TYLVALOSIN AS ANTIVIRAL AGENT

The present application is a Divisional of U.S. application Ser. No. 12/373,657 filed Mar. 31, 2009, now U.S. Pat. No. 9,066,964, which is a U.S. National Phase of International Application No. PCT/GB07/02620, filed on Jul. 13, 2006, which claims priority to GB0613952.1, filed Jul. 13, 2006, and GB0621782.2, filed Nov. 1, 2006, the entire contents of each are incorporated herein by reference.

The invention relates to the use of an antibiotic in the preparation an antiviral medicament. The invention also relates to a method of treating a viral infection comprising administering an antibiotic to a subject having a viral infection.

Tylvalosin is the provisional INN name for acetylisovaleryltylosin and is a macrolide antibiotic. The product containing tylvalosin is known as Aivlosin®. It is used in a variety of treatments, particularly for treating various bacterial infections in farm animals. Tylvalosin is a derivative of tylosin and has the following formula:

[Chemical structure of tylvalosin]

in which R is isovaleryl.

When livestock animals are reared in large-scale operations, especially intensive operations, they have a tendency to suffer from certain diseases. Such diseases also tend to spread rapidly through the livestock. One such disease is porcine reproductive and respiratory syndrome (PRRS). PRRS is caused by a virus, PRRSV, and affects pigs of all ages. It has both respiratory and reproductive signs and is thought to cost the worldwide pig industry hundreds of millions of pounds sterling each year.

PRRS is often complicated by a bacterial infection, particularly an infection with *Mycoplasma hyopneumoniae* (M-hyo). This infection is widespread in pig populations and causes pneumonia. When a pig is infected with both M-hyo and PRRSV, the pneumonia can become very severe. At present, Aivlosin® (tylvalosin) is used to treat M-hyo, in pigs with and without PRRS.

The inventors have surprisingly found that Aivlosin® (tylvalosin) can be used to treat PRRSV itself. The inventors have found that Aivlosin® (tylvalosin) has a direct effect on the virus.

Up to now, Aivlosin® has only been used to treat bacterial infections such as M-hyo. Aivlosin® (tylvalosin) has not been used to treat viral infections. Although Aivlosin® (tylvalosin) has been used to treat M-hyo in pigs with PRRS, it was not known that it could have an effect on the virus as well as on the bacterial infection.

It is not usual for antibiotics to have an effect on viral infection. Tylvalosin is a macrolide antibiotic. Other macrolides have very varied effects on viruses. Tilmicosin has been shown to be effective against some viruses, including PRRSV. However, tilmicosin is much more toxic than tylvalosin in cell culture assays of antiviral potency. Further, tylosin, the antibiotic to which tylvalosin is most closely related has no effect on PRRSV and is not known to have any effect on other viruses.

In accordance with the invention, there is provided the use of tylvalosin, or a functional derivative, metabolite, ester or salt thereof, in the preparation of a medicament for the prevention or treatment of an infection with a virus.

As indicated above, tylvalosin is a macrolide antibiotic called 3-O acetyl-4"-O-isovaleryltylosin. Tylvalosin is well known in the art. Derivatives and metabolites of tylvalosin include any compounds closely related to tylvalosin or which tylvalosin becomes when in solution or when administered to a subject. Derivatives and metabolites of tylvalosin include a number of compounds found as related substances in tylvalosin, especially in solution, such as 3-O-Acetyldesmycosin, 3-O-Acetyltylosin, 3,4"-di-O-Acetyltylosin, 3-O-Acetyl-4"-O-propionyltylosin, 3-O-Acetyl, -4"-O-Isovalerylmacrocin, 3-O-Acetyl-4"O-butyltylosin, 3-O-Acetyl-4"-O-isovalerylrelomycin, 4"-O-Isovaleryltylosin, 3,20-di-O-Acetyl-4"-isovalerylrelomycin, and 3,4'"-di-O-Acetyl-4"-O-isovaleryltylosin. Tylvalosin may be in the form of Aivlosin®.

When tylvalosin is present in the form of a pharmaceutically acceptable ester, an alkyl ester thereof is preferred. When tylvalosin is present in the form of a pharmaceutically acceptable salt, any appropriate salt may be used. Salts formed with organic acids are preferred, especially salts formed with acids such as ascorbic, glycolic, lactic, malic, tartaric or citric acid.

Functional derivatives, metabolites, esters and salts function in the same way as tylvalosin, that is to say, they have a similar effect on a particular viral infection.

It is particularly preferred that the invention relates to the use of tylvalosin, or an ester or salt thereof, in the preparation of a medicament for the prevention or treatment of an infection with a virus.

The term infection with a virus means the presence in a host of viral particles. In particular, it means the presence in a subject of viral particles not normally found in that host or of viral particles that are pathogenic or cause disease in the host.

Prevention of an infection with a virus means that there is a reduction of the number of viral particles in a host, or reduction or prevention of replication of viral particles in a host, or reduction or prevention of the cytopathic effect of virus reproduction, or reduction or prevention of entry of the virus into the cell cytoplasm, or the reduction or prevention of pathological effects or signs/symptoms of the viral infection, when compared to the expected status of an untreated host following exposure to the virus.

An untreated host is a host that has not received the medicament prepared in accordance with the invention.

The expected status is the likely number of viral particles, or level of cytopathic effects, or pathological effects or signs/symptoms in an untreated host following exposure to the virus. One skilled in the art would be able to predict this.

Treatment of an infection with a virus means that there is a reduction of the number of viral particles in a host, or reduction or prevention of replication of viral particles in a host, or reduction or prevention of the cytopathic effect of virus reproduction, or reduction or prevention of entry of the virus into the cell cytoplasm, or the reduction or prevention of pathological effects, clinical signs or symptoms of the viral infection, when compared to the status prior to treatment.

Where there is a reduction of the number of viral particles in a host, or reduction of replication of viral particles in a host, or reduction of the cytopathic effect of virus reproduction, or reduction of entry of the virus into the cell cytoplasm, or reduction of pathological effects, clinical signs or symptoms of the viral infection, the reduction is preferably statistically significant. For example, there is preferably a reduction of at least 25%, more preferably at least 30%, even more preferably at least 35%, most preferably at least 40%.

A host is a higher organism, the cells of which are used by the virus for replication. The host may be a human or an animal. It is preferred that the host is an animal, especially a livestock animal such as a cow, horse, poultry or pig. It is particularly preferred that the host is a pig. Alternatively, the host is preferably a human.

The virus is preferably a virus that uses the endosomal or lysosomal pathway to infect host cells.

The terms endosomal pathway and lysosomal pathway are well known in the art. They refer to mechanisms used by some viruses to enter cells. All viruses must have ways of entering target cells in order to initiate replication. Viruses generally do this in two ways, either by a direct mechanism at the cell's plasma membrane, or following internalisation into a cellular compartment such as an endosome or a lysosome. Viruses that use endosomes and lysosomes to enter the cell must also fuse with or penetrate the endosomal or lysosomal membrane in order to be released into the cell cytoplasm.

An endosome is an organelle that carries materials newly ingested by endocytosis. The term is well known in the art.

A lysosome is an organelle that contains degradative enzymes. The term is well known in the art.

Many viruses that use the endosomal or lysosomal pathway require a specific pH in order to undergo a conformational change that triggers fusion with the endosomal membrane and cell entry.

Without being bound by a particular theory, it is the inventors' belief that tylvalosin enters cells and concentrates in endosomes and lysosomes and affects the pH in those endosomes and lysosomes. The inventors believe that this change in the endosome or lysosome pH prevents the fusion of viral particles within the endosome or lysosome with the endosome or lysosome membrane and hence prevents the virus from entering the cell cytoplasm and replicating.

The virus is preferably a virus that uses the late endosomal pathway or lysosomal pathway.

A late endosome is a pre-lysosomal organelle. The term late refers to the amount of time it takes for endocytosed molecules to be delivered to the late endosome. Late endosomes are more spherical than early endosomes and are positioned dose to the nucleus. Late endosomes have a more acidic pH than early endosomes. The term late endosome is well known in the art.

The virus is preferably a virus that uses an endosomal or lysosomal pathway controlled by Rab7.

Rab proteins are small GTPases found at the cytoplasmic face of certain cellular compartments. They have a role in the regulation of trafficking across the membrane of those compartments. Rab7 has a role in the regulation of trafficking in late endosomes and lysosomes.

The virus is preferably a virus that requires a pH within the endosome or lysosome of below 6.5, preferably below 6, more preferably below 5.5, even more preferably below 5, most preferably below 4.5.

The pH of the endosome or lysosome can be measured using a pH sensitive dye, for example one which fluoresces blue at neutral pH and yellow/green at low pH. The ratio of blue:yellow provides a measure of the endosome/lysosome pH (Diwu, Chen, Zhang, Klaubert and Haughland (1999) Chemistry and Biology Vol 6 Issue 7 411-418).

It is generally known whether a virus uses the endosomal or lysosomal pathways to achieve cell entry. In the unlikely event that it is not known, one skilled in the art can confirm whether a virus uses the endosomal or lysosomal pathway, check which part of the pathway is used or confirm pH or Rab protein dependence by testing viral entry into cells in the presence of compounds that are known to alter endosomal or lysosomal pH, or by using mutants that are negative for a particular Rab protein. For example, the following chemical inhibitors may be used:

Chloroquine and ammonium chloride, which raise endosomal pH by acting as proton sinks; and Nocodazole, which depolymerises microtubules and blocks transition from early endosome to late endosomes.

If a virus does not achieve cell entry in the presence of chloroquine or ammonium chloride, it can be considered to be pH dependent, requiring an acidic pH to infect cells. If a virus is prevented from infecting cells by nocodazole, it can be considered to use the late endosome pathway or lysosome pathway to enter cells, its entry to these pathways being blocked by the nocodazole. Alternatively, the following dominant negative mutants may be used:

rab5 S34N mutant, which blocks transition from clathrin coated pits in the plasma membrane to early endosomes, and rab7 T22N mutant, which blocks transition from early endosomes to late endosomes.

Viruses inhibited by the rab5 S34N mutant require passage through an early endosome, at about pH 6.5. Viruses inhibited by the rab7 T22N mutant require passage through a late endosome at about pH 5.

The virus may be, for example, a virus from any of the following families: Adenoviridae, Arteriviridae, Asfarviridae, Bunyaviridae, Circoviridae, Coronaviridae, Filoviridae, Flaviviridae, Orthomyxoviridae, Parvoviridae, Picornaviridae, Reoviridae, and Togaviridae.

Further, the virus may be, for example, a virus from any of the following genera: Mastadenovirus, Arterivirus, Asfarvirus, Hantavirus, Circovirus, Coronavirus, Flavivirus, Pestivirus, Hepacivirus, Influenza virus A, Isavirus, Parvovirus, Enterovirus, Rhinovirus, Orthoreovirus, Rotavirus, and Alphavirus.

In particular, the term virus may mean any one or more of, or any combination of adenovirus 7, PRRSV, influenza, including human, avian, swine, horse, bovine and dog influenza, salmon anaemia virus, classical swine fever, Hepatitis C virus, Hepatitis E virus, African swine fever virus, Puumala virus, infectious bronchitis virus, transmissible gastroenteritis, SARS CoV, Mraburg virus, Ebola virus, West Nile virus, yellow fever virus, tick borne encephalitis virus, bovine diarrhoea virus, canine parvovirus, Coxsackie B3, Coxsackie B5, avian reovirus, rotavirus, Semliki forest virus and porcine circo type 2.

The virus is preferably PRRSV.

Alternatively the virus is preferably not PRRSV.

In another alternative, the virus is preferably influenza, especially human influenza, particularly human influenza strain A or B, especially strain A.

Details of preferred viruses are given in Table 6.

Further, the invention provides the use of tylvalosin or a functional derivative, metabolite, ester or salt thereof in the preparation of a medicament for the treatment of any one or more of, including any combination of, adenovirus 7, PRRSV, influenza, including human, avian, swine, horse, bovine and dog influenza, salmon anaemia virus, classical swine fever, Hepatitis C virus, Hepatitis E virus, African swine fever virus, Puumala virus, infectious bronchitis virus, transmissible gastroenteritis virus, SARS CoV, West Nile virus, Marburg virus, Ebola virus, yellow fever virus, tick borne encephalitis virus, bovine diarrhoea virus, canine parvovirus, Coxsackie B3, Coxsackie B5, avian reovirus, rotavirus, Semliki forest virus and porcine circo type 2.

Additionally, the invention provides the use of tylvalosin, or a functional derivative, metabolite, ester or salt thereof, in the preparation of a medicament for the prevention or treatment of an infection with a virus as defined herein and the prevention or treatment of a bacterial infection.

The prevention or treatment of an infection with a virus may be simultaneous with, or subsequent or prior to the prevention or treatment of a bacterial infection.

The term bacterial infection means the presence in a host of bacteria. In particular, it means the presence in a subject of bacteria not normally found in that host or of bacteria that are pathogenic or cause disease in the host or the presence of such bacteria in a location within the host in which the bacteria are not normally found.

Prevention of a bacterial infection means that there is a reduction of the number of bacteria in a host, or reduction or prevention of replication of bacteria in a host, or the reduction or prevention of pathological effects or clinical signs or symptoms of the bacterial infection, when compared to the expected status of an untreated host following exposure to the bacteria.

An untreated host is a host that has not received the medicament prepared in accordance with the invention.

The expected status is the likely number of bacteria or pathological effects or clinical signs or symptoms in an untreated host following exposure to the bacteria. One skilled in the art would be able to predict this.

Treatment of a bacterial infection means that there is a reduction of the number of bacteria in a host, or reduction or prevention of replication of bacteria in a host, or the reduction or prevention of pathological effects or clinical signs or symptoms of the bacterial infection, when compared to the status prior to treatment.

The bacterial infection may be any infection that is susceptible to treatment with tylvalosin or a functional metabolite, derivative, ester or salt thereof. In particular the bacterial infection may be an infection with any one or more of the following bacteria:

*Mycoplasma* species (*M. hyopneumoniae, M. hyosynoviae, M. hyorhinis M. gallisepticum, M. synoviae, M. meleagridis, M. bovis, M. bovirhinis*)

*Orninthobacterium rhinotracheale*

*Bordetella bronchiseptica*

*Actinobaccilus pleuropneumoniae*

*Pasteurella multocida*

*Mannheimia* (*Pasteurella*) *haemolytica*

*Rhodococcus* (*Corynebacterium*) *equi*

*Streptococci* (*Strep. suis, Strep. pyogenes,*)

*Staphylococci* (*Staph. aureus, Staph. epidermidis,*)

*Brachyspira hyodysenteria*

*Brachyspira pilosicoli*

*Lawsonia intracellularis*

*Clostridium perfringens*

(*Clostridium* species)

*Corynebacterium diptheriae*

*Aerococcus catalasicus*

*Alcaligenes viscolactis*

*Micrococcus luteus*

*Microbacterium flavum*

*Bacillus subtilis*

*Bacillus circulans*

*Bacillus licheniformis*

*Rickettsia* spp

*Chlamydia* spp

*Listeria* spp

*Erysipelothrix rhusiopathiae*

*Bartonella henselae*

*Helicobacter pylori*

*Streptococcus agalactiae, Strep. uberis*

*Fusobacterium necrophorum*

*Leptospira* spp

The bacterial infection is preferably an infection with a *mycoplasma* species, especially *Mycoplasma hyopneumoniae.*

A number of viral infections are often seen in conjunction with other viral infections and/or bacterial infections and it is particularly useful to be able to use one medicament to treat more than one of the infections. For example, one of the most important economical diseases of commercial pig production is a disease that has been called Porcine Respiratory Disease Complex (PRDC). It is multifactorial and a number of viruses and bacteria are involved, including PRRSV, porcine circovirus type 2, swine influenza, porcine coronavirus and pseudorabies virus (Aujeszky's) and the bacterial pathogens *Mycoplasma hyopneumoniae, Actinobacillus pleuropneumoniae, Pasteurella multocida, Streptococcus suis* and *Bordetella brochiseptica*. Accordingly, when the viral infection is an infection with PPRSV and/or swine influenza, the bacterial infection is preferably an infection with one or more of *Mycoplasma hyopneumoniae, Actinobacillus pleuropneumoniae, Pasteurella multocida, Streptococcus suis* or *Bordetella brochiseptica.*

In cattle there is a similar respiratory disease complex associated with bovine virus diarrhoea virus (BVD), parainfluenza (PIV), bovine respiratory syncytical virus (BRSV), infectious bovine rhinotracheitis (IBR) and *Pasteurella. Mycoplasma bovis* may also exacerbate this disease.

Accordingly, when the viral infection is an infection with bovine virus diarrhoea virus, the bacterial infection is preferably an infection with *Mannheimia (Pasteurella) haemolytica* or *Mycoplasma bovis.*

There are a number of low pathogenic avian influenza viruses in poultry and these have been associated with much increased disease when *Mycoplasma gallisepticum* is also present. High mortality and morbidity is seen in dually-infected flocks.

Accordingly, when the viral infection is an infection with avian influenza, the bacterial infection is preferably an infection with *Mycoplasma gallisepticum.*

Influenza virus infection in man can predispose the individual to secondary bacterial infections such as *Staphylococcus aureus, Streptococci haemolyticus, Pneumococci, Pseudomanoas aeroginosa, Haemophilus influenzae.*

Accordingly, when the viral infection is an infection with human influenza, the bacterial infection is preferably an infection with one or more of *Staphylococcus aureus, Streptococci haemolyticus, Pneumococci, Pseudomanoas aeroginosa,* and *Haemophilus influenzae.*

*Mycoplasma pneumoniae* is a common cause of respiratory disease and co-infections with influenza virus and respiratory syncytial virus have been reported, as has the fact that *M. pneumoniae* can superinfect during an influenza outbreak.

Hence, alternatively, when the viral infection is an infection with influenza, the bacterial infection is preferably an infection with *Mycoplasma pneumoniae.*

Also provided is a method of preventing or treating a viral infection comprising administering tylvalosin or a functional derivative, metabolite, ester or salt thereof, or a pharmaceutical composition comprising tylvalosin or a functional derivative, metabolite, ester or salt thereof, to a subject having a viral infection.

The method may also be used for simultaneously treating or preventing a bacterial infection.

A pharmaceutical composition to be administered in the method of the invention comprises tylvalosin or a functional derivative, metabolite, ester or salt thereof with any pharmaceutically acceptable carrier, adjuvant or vehicle. Pharmaceutically acceptable carriers, adjuvants and vehicles that may be used in the pharmaceutical composition include, but are not limited to, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical composition may be administered orally, parenterally, by inhalation spray, rectally, nasally, buccally, vaginally, topically, transdermally or via an implanted reservoir. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical composition may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical composition may also be administered in the form of suppositories for rectal administration. These compositions can be prepared by mixing a compound of this invention with a suitable non-irritating excipient, which is solid at room temperature but liquid at the rectal temperature and therefore will melt in the rectum to release the active components. Such materials include, but are not limited to, cocoa butter, beeswax and polyethylene glycols.

The pharmaceutical composition may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The subject may be any subject having a viral infection. In particular, the subject may be a human or an animal. It is preferred that the host is an animal, especially a livestock animal such as a cow, horse, poultry or pig. It is particularly preferred that the host is a pig. Alternatively, the host is preferably a human.

The invention will now be described in detail, by way of example only, with reference to the figures, in which, FIG. 1 shows the results of an assay for the number of cells that are infected following exposure to PRRSV, in the presence of Aivlosin® (tylvalosin);

FIG. 2 shows the results of an assay for the number of MDCK cells that are infected following exposure to influenza, in the presence of Aivlosin® (tylvalosin);

FIG. 3 the results of an assay for the number of Caco-2 cells that are infected following exposure to influenza, in the presence of Aivlosin® (tylvalosin);

FIG. 4 shows the results of an assay for the number of HeLa cells that are infected following exposure to influenza, in the presence of Aivlosin® (tylvalosin);

FIG. 5 shows the effect of time and concentration on the intracellular accumulation of tylvalosin in HRT-18 cells. a) HRT-18 cells were incubated with 0.5, 5 or 50 µg/mL tylvalosin for either 4 or 24 h. Samples of medium (white and light grey bars) and cells (black and dark grey bars) were harvested in duplicates. Concentrations in the medium are shown as µg/ml tylvalosin/mL medium whilst those from the cells are µg tylvalosin/mg cells. b) The ratio of the intracellular:extracellular concentrations of tylvalosin were calculated for each sample (sample 1 in the black bars and sample 2 in the white bars) and plotted;

FIG. 6 shows intracellular accumulation of tylvalosin, tylosin and tilmicosin in HRT-18 cells. a) HRT-18 cells were incubated with 10 µg/mL each antibiotic for 4 or 24 h. Duplicate samples of cells were harvested at each time point (white and black bars) and a sample of medium was harvested (grey bars). Concentrations in the medium are shown as µg macrolide/ml medium whilst those from the cells are µg macrolide/mg cells. b) intracellular:extracellular concentration ratios of each macrolide were calculated and plotted (sample 1 in the black bars and sample 2 in the white bars);

FIG. 7 shows intracellular accumulation and transepithelial transport of tylvalosin in polarised Caco-2 cells. Caco-2 cells were incubated with 100 µg/mL tylvalosin in either the apical (a) or basolateral (b) chambers for 30 (light grey bars), 60 (black bars), 120 (white bars) and 240 (dark grey bars) minutes. Duplicate samples of cells and medium from both chambers were harvested at each time point. Concentrations in the medium are shown as µg tylvalosin/ml medium whilst those from the cells are µg tylvalosin/mg cells. Intracellular:extracellular concentration ratios of samples where tylvalosin was added in the apical (c) and basolateral (d) chambers were calculated and plotted (sample 1 in the black bars and sample 2 in the white bars). Medium from the basolateral chamber after apical administration (e) and the apical chamber after basolateral administration (f) was sampled and the concentration of tylvalosin was plotted as a percentage of the input;

FIG. 8 shows intracellular accumulation and transepithelial transport of tylvalosin, tylosin and tilmicosin in polarised Caco-2 cells. a) Caco-2 cells were incubated with 10 µg/mL tylvalosin, tylosin or tilmicosin in the apical for 30 (light grey bars), 60 (black bars), 120 (white bars) and 240 (dark grey bars) min. Duplicate samples of cells and medium from both chambers were harvested at each time point. Concentrations in the medium are shown as µg macrolide/ml medium whilst those from the cells are µg macrolide/mg cells. b) Intracellular:extracellular concentration ratios of samples were calculated and plotted (sample 1 in the black bars and sample 2 in the white bars). c) Medium from the basolateral chamber after apical administration was sampled and the concentration of antibiotic was plotted as a percentage of the input;

FIG. 9 shows intracellular accumulation of tylvalosin, tylosin and tilmicosin in pig kidney epithelial cells. a) LLC-PK1 cells were incubated with 10 µg/mL each antibiotic for the times shown in the key. Duplicate samples of cells and medium were harvested at each time point (grey bars for 32 min, white bars for 75 min and black bars for 120 min samples). Concentrations in the medium are shown as µg macrolide/mL medium whilst those from the cells are µg macrolide/mg cells. b) Intracellular:extracellular concentration ratios of each macrolide were calculated and plotted (grey bars for 32 minutes, white bars for 75 min and black bars for 120 min samples); and FIG. 10 shows intracellular accumulation of macrolide antibiotics in pig and chicken white blood cells. a) Pig white blood cells were incubated with 10µ/mL tylvalosin or tylosin for 10 or 20 min. Cells loaded with macrolide after 20 min incubation were transferred to medium and incubated for a further 30 min. Duplicate samples of cells and medium were harvested at each time point (grey bars for 10 min, white bars for 20 min and black bars for 30 min washout). Concentrations in the medium are shown as µg macrolide/mL medium whilst those from the cells are µg macrolide/mg cells. b) Intracellular:extracellular concentration ratios of each macrolide were calculated and plotted (grey bars for 10 min and white bars for 20 min). c) The amount of macrolide remaining in the cell after washout was assessed and the % retention in the cell was calculated and plotted (black bars for 30 min washout samples). d) Chicken white blood cells were incubated with 10 µg/mL tylvalosin, tylosin or tilmicosin for 15, 30 or 60 min. Duplicate samples of cells and medium were harvested at each time point (grey bars for 15 min, white bars for 30 min and black bars for 60 min). Concentrations in the medium are shown as µg macrolide/mL medium whilst those from the cells are µg macrolide/mg cells. e) intracellular:extracellular concentration ratios of each macrolide were calculated and plotted (grey bars for 15 min, white bars for 30 min and black bars for 60 min).

EXAMPLES

Example 1

PRRSV Assay

Figure 1:
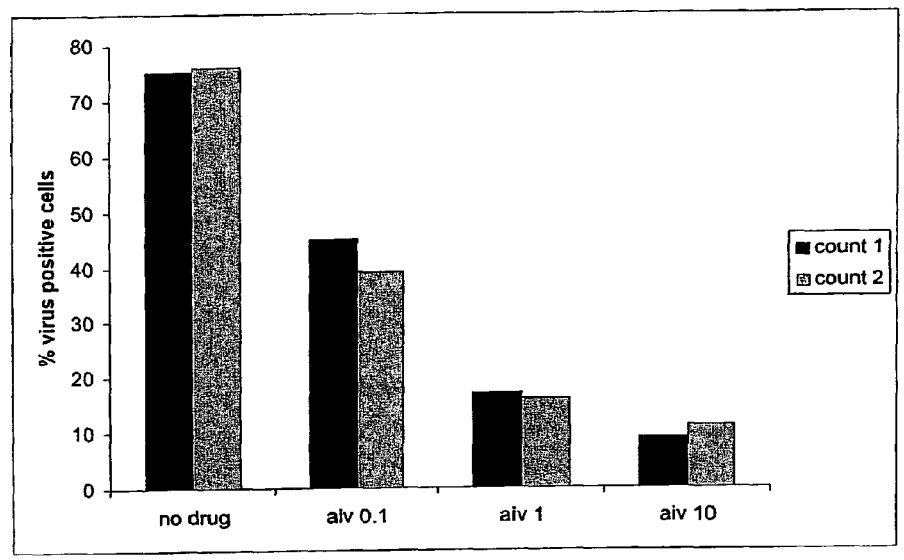
Figure 2:
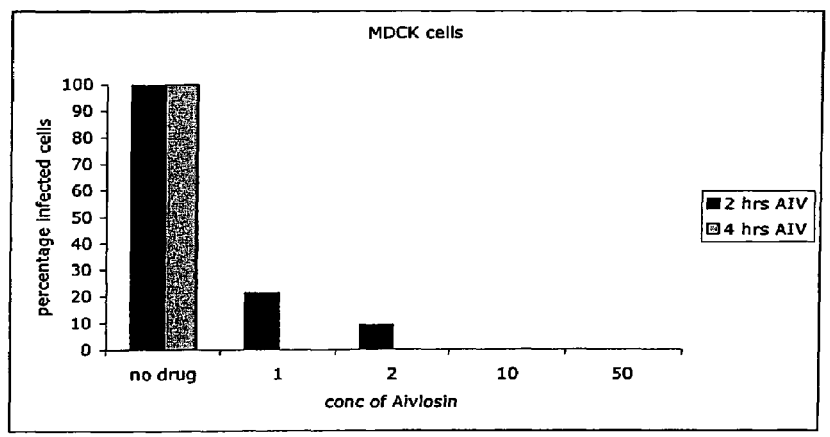
Figure 3:
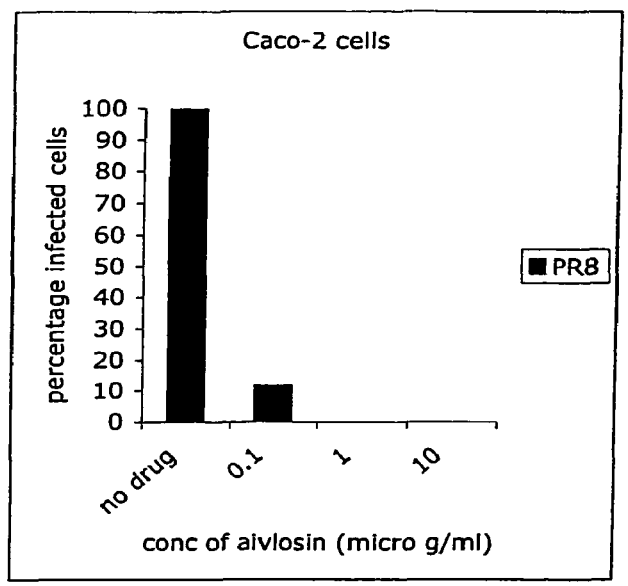
Figure 4:
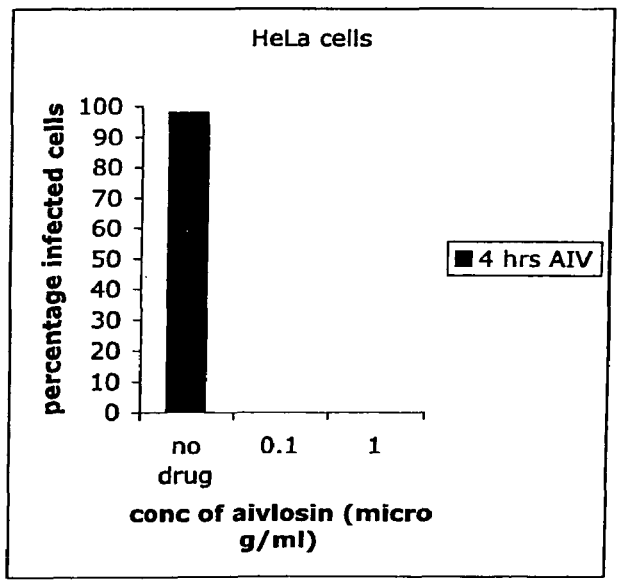

MA104 cells were pre-treated with Aivlosin® (tylvalosin) or tilmicosin for four hours. Cells were then exposed to PRRSV in the presence of the tylvalosin or tilmicosin. Cells were then washed three times with PBS to remove unbound virus and fresh medium containing tylvalosin or tilmicosin was added. The cells were incubated for a further 24 hours before being fixed with 4% formaldehyde. Virus infection was detected by indirect immunofluorescence using porcine polyclonal anti-PRRSV primary antibodies and FITC-labeled anti-porcine secondary antibodies. Immunofluorescence was detected using a Leica confocal microscope. Cells showing green fluorescence (from the FITC staining) were scored as positive per DAPI stained nucleus.

Example 2

Influenza Assays

Tylvalosin was added to MDCK, HeLa or CaCo-2 cells for 2 or 4 hours at varying concentrations. Cells were then exposed to PR8 strain of influenza A virus (multiplicity of infection of 10). Cells were then fixed with 4% formaldehyde after 4 hours and stained for influenza nucleoprotein (NP) using rabbit anti-NP primary antibodies and Alexa Fluor 488 anti-rabbit secondary antibodies. Immunofluorescence was detected using a Leica confocal microscope. Cells showing green fluorescence (from the Alexa Fluor 488 staining) were scored as positive per DAPI stained nucleus.

Example 3

Comparison of Intracellular Accumulation and Trans-Epithelial Transport of Aivlosin, Tylosin and Tilmicosin The macrolide antibiotics tylvalosin, tilmicosin and tylosin were tested for their ability to enter and accumulate inside three cell types, epithelial (gut, kidney) and white blood. Tylvalosin (3-acetyl4-isovaleryltylosin) rapidly entered all the three cell types and the greatest concentration was obtained in the cytoplasm of white blood cells. It also entered polarized Caco-2 epithelial cells by either the apical or basolateral surface, to be concentrated inside the cells and to be transported to the opposite surface. Tylosin entered all cell types relatively poorly, whilst tilmicosin was intermediate in its ability to enter and accumulate in cells. The greater uptake by tylvalosin may be related to the presence of an isovaleryl group. Although the three antibiotics are all macrolides, they were shown to differ in at least one aspect of distribution, relevant to their efficacy in treating clinical disease.

Macrolide antibiotics are known to penetrate cells and to be concentrated within them. The weakly basic antibiotic becomes trapped in the acidic environment in cells, especially in the lysosomes (Tulkens, 1991) and may also be concentrated in other intracellular organelles. However, the extent of intracellular penetration and concentration varies between macrolides and between cell types (Bosnar et al., 2005, Labro, 1993). Tilmicosin has previously been reported to concentrate in cells (Scorneaux and Shrycock, 1998a,b).

Three macrolide antibiotics with similar efficacy claims are acetylisovalerytylosin (Tylvalosin, ECO Animal Health), tylosin (Tylan, Elanco Animal Health) and tilmicosin (Pulmotil, Elanco Animal Health). Tylvalosin has recently been approved throughout the European Union (EU), via the centralised procedure, for the treatment and prevention of enzootic pneumonia (*Mycoplasma hyopneumoniae*) in pigs, for the treatment of ileitis (*Lawsonia intracellularis*) and for the treatment and prevention of swine dysentery (*Brachyspira hyodysenteriae*). It is used in certain non-EU countries for the treatment and prevention of mycoplasmosis (*Mycoplasma gallisepticum, Mycoplasma synovae*) in chickens. Tilmicosin is used in pigs for the treatment of pneumonia caused by *Mycoplasma hyopneumoniae* and for the treatment of respiratory infections in chicken flocks associated with *Mycoplasma gallisepticum*. Tylosin is used for the prevention and control of enzootic pneumonia, for the prevention and control or treatment of swine dysentery and for the treatment and control of *Lawsonia intracellularis*. It is also used for the control of *Mycoplasma gallisepticum* strain S6 in chickens.

Hence, enterocytes and respiratory epithelial cells appear to be the target for these pathogens. There are several reports of the effect of macrolides on the innate or non-specific immune system (Ianaro et al., 2000; Labro, 1993; Labro, 2000; Sunazuka et al., (2003)). The two major phagocytic cell types in the body involved in combating microbial diseases are macrophages and neutrophils (heterophils in chickens). Whereas macrophages, derived from blood monocytes, are relatively long-lived cells, neutrophils are short-lived. It is known that both cell types are important in the innate immune system.

The uptake and concentration of the three antibiotics in various cells types, representing enterocytes, epithelial cells and white blood cells (WBCs), was investigated. The investigation used established human gut epithelial cell lines (HRT-18 and Caco-2) as both of these cell types retain some of the properties of in-vivo enterocytes. Caco-2 cells can form polarized monolayers (in that they have an apical surface and a basolateral surface) when grown on a semi-permeable membrane. Medium can be placed both above and below the semi-permeable membrane and the trans-epithelial transport of molecules can be studied using these cells. Enterocytes are involved in the uptake of antibiotics from the gut (intestinal lumen). Pig kidney cells were used as an example of an epithelial cell type and both chicken and pig WBCs were also used.

Materials and Methods
Antibiotic Stock Solutions
Tylvalosin was obtained in the tartrate form as the water-soluble product (ECO Animal Health). The active ingredient tylvalosin (3-acetyl4-isovaleryltylosin) comprises 70.71% of tylvalosin granules for oral solution, according to the certificate of analysis. Throughout this report, tylvalosin refers to the active ingredient, acetylisovaleryltylosin. Tylosin, in the form of Tylan Soluble, (ELANCO Animal Health) was used as the tartrate salt. Tilmicosin, in the form of Pulmotil AC (ELANCO Animal Health) was used. Tilmicosin is derived from a fermentation product of fraction B of tylosin.

Cell Lines
HRT-18, Caco-2 and LLC-PK1 cells were obtained from ECACC. HRT-18 cells were maintained in RPMI 1640 media containing 10% foetal calf serum, 100 U/mL penicillin and 100 µg/mL streptomycin. Caco-2 cells were maintained in DMEM supplemented with 10% foetal calf serum, 2 mM L-glutamine and 100 U/mL penicillin and 100 µg/mL streptomycin. LLC-PKI cells were maintained in Medium 199 containing 10% foetal calf serum, 2 mM L-glutamine, 100 U/mL penicillin and 100 µg/mL streptomycin.

Preparation of Pig and Chicken White Blood Cells
Pig blood was collected in Heparin-coated BD vacutainers (6). 20 mL of blood and 30 mL of phosphate buffered saline (PBS) were mixed in a 50 mL conical centrifuge tube. This was repeated in order to obtain 3 such tubes. The mixtures were centrifuged for 10 min at 2050×g. The white blood cells, together with some red blood cells below, were harvested into a 50 mL conical centrifuge tube. PBS was added to about 50 mL. A 63% solution of Percoll was made as follows: 6.3 mL Percoll (Sigma), 1.0 mL 1.5 M NaCl, 2.7 mL $H_2O$. 10 mL of 63% Percoll was added to each of two 50 mL conical centrifuge tubes. 25 mL of the resuspended white blood cells were carefully layered on top of the each of the Percoll solutions. A sharp interface was produced. The material was centrifuged at 3000×g for 10 min. A clear band of white blood cells was seen at the PBS/Percoll interface. The white blood cells were harvested in PBS (50 mL) and centrifuged at 500×g for 10 min. The cell pellet was resuspended in medium (Glasgow minimum essential medium containing penicillin and streptomycin). A viable cell count was made using trypan blue. The same method used for isolation of pig WBCs was used for the chicken WBCs, with the exception that heparin (100 I.U./mL) was prepared and mixed with an equal volume of chicken whole blood.

Time and Concentration Effects for the Intracellular Accumulation of Tylvalosin in HRT-18 Cells HRT-18 cells, in 6 cm tissue cultures dishes, were incubated in the presence of 0.5, 5 or 50 μg/mL tylvalosin. After 4 h, two dishes for each tylvalosin concentration and two dishes without antibiotic were removed from the incubator. A sample of medium (about 1 mL) was removed, placed in a labelled Eppendorf tube and stored at −20° C. The rest of the medium was then removed. Each of the cell monolayers was washed twice in PBS, using approximately 5 mL for each wash. The plunger from a 2 mL plastic syringe was used to gently scrape off the cells. PBS (500 μL) was added to the dish and the cells gently removed into this medium, using a micropipette. The sample was then placed in an Eppendorf tube and centrifuged at 8000×g in a bench centrifuge (Biofuge pico, Heraeus instruments) for 13 sec. An obvious cell pellet formed. The supernatant was removed using a micropipette and the cell material was stored at −20° C. in a labelled Eppendorf tube. After approximately 24 h the remaining tissue culture dishes were removed from the incubator and treated as described above for the 4 h samples. All the samples, including the 4 h samples, were then stored at −70° C.

Intracellular Accumulation of Tylvalosin, Tylosin and Tilmicosin in HRT-18 Cells HRT-18 cells were prepared as described above and used at passage 42. Stock solutions of antibiotics (either tylvalosin, tylosin or tilmicosin) were diluted in growth media and 10 μg/mL each antibiotic was added to the confluent cell monolayers. The cells were incubated at 37° C. in a 5% $CO_2$ atmosphere for either 4 h or 24 h. The media and cells were harvested and tested for antibiotic, as described above.

Intracellular Accumulation and Trans-Epithelial Transport in Caco-2 Cells

Caco-2 cells were seeded at a density of 0.8×10⁶ cells per well of a Transwell Clear filter 6 well plate, 0.4 μm pore size. The cells were incubated with 2 mL medium in both apical and basolateral chambers. This medium was replaced every 2 days for 10-14 days. Transepithelial resistance was measured using Millicell ERS apparatus (Millipore) at day 7, 10 and/or 14 in order to identify when the cells had become polarised. Readings of >1000 Ω were indicative of polarised cells. The different drugs (at 100 μg/mL) were placed in the apical or basolateral chambers and at various times points, up until 240 min, the medium in both the apical and basolateral compartments and the cells were harvested and analysed for macrolide content.

Intracellular Accumulation of Tylvalosin, Tylosin and Tilmicosin in Pig Kidney Cells LLC-PKI cells in 6 cm² plastic tissue culture dishes were incubated with 10 μg/mL of the different macrolides. Cells and medium were harvested as described above at 30, 75 and 120 min.

Intracellular Accumulation of Tylvalosin, Tylosin and Tilmicosin in Pig White Blood Cells and Chicken White Blood Cells Cells were incubated with 10 mg/mL of each antibiotic. All tubes were placed on a rotary mixing machine, at 37° C. Supernatant and cell samples were harvested at the times described in the figure legends. Duplicate samples were used for each antibiotic for each time point.

Analysis of Samples Containing Tylvalosin, Tylosin and Tilmicosin

All the supernatant and cell samples were transported frozen (at approximately −20° C.) to York Bioanalytical Solutions (York, England) for analysis. Briefly, 0.25 g of buffer (RPMI medium containing 10% FCS) was weighed into a polypropylene tube. A 50 μL volume of the appropriate working solution was added to the quality control (QC) samples. Methanol (50 μL) was added to each blank sample used for preparation of calibration standards, recovery samples and reagent blanks. A 2.5 mL volume of 0.1 M phosphate buffer was added to each sample, vortex mixed for approximately 1 min and then centrifuged at 3220×g for 10 min at 4° C.

For the liquid-liquid clean-up phase, an aliquot (100 μL) of the supernatant was transferred to a polypropylene tube. The pH was adjusted to pH 8-8.5 by the addition of 0.1 M NaOH, and vortex mixed. Ethyl acetate (5 mL) was added and after capping, the whole mixture was shaken for 10 min and then centrifuged at 3220×g for 10 min at 4° C.

Ammonium acetate (20 mM; pH native)—formic acid, 1000:3, v/v (100 μL) was added to each well in a 2 mL polypropylene collection plate. An aliquot of the ethyl acetate mixture (100 μL) was transferred to the polypropylene collection plate and evaporated under nitrogen (40° C.) until the ethyl acetate was fully evaporated whilst the ammonium acetate remained. Methanol (100 μL) was added to each well, excluding the calibration standards.

To each well containing a calibration standard, 100 μL of the appropriate calibration working solution was added. Samples were then vortex mixed for at least 10 min and submitted for liquid chromatography with tandem mass spectrometric analysis. The method stated was applicable to the samples of media (and the calibration standards and quality control samples).

For the cells, the sample tubes were weighed, and 100 μL of acetonitrile was added. The samples were vortex mixed for 10 sec, then centrifuged at 10285×g at 4° C. for 5 min. The sample was transferred to a polypropylene tube. The original sample tube was washed with 0.1 M phosphate buffer (1 mL). This was transferred to the polypropylene tube. A second wash of 1 mL was made, then a final wash of 0.5 mL. The polypropylene tube was now at the same stage as the end of the liquid extraction, but with the cells present rather than media. This was then taken through the sample preparation as described above. The original sample tubes were allowed to dry (i.e. any remaining solvent evaporated off) and were then reweighed to determine the weight of cells in the sample, to allow the concentration per gram of cells to be determined.

Results

Figure 5:
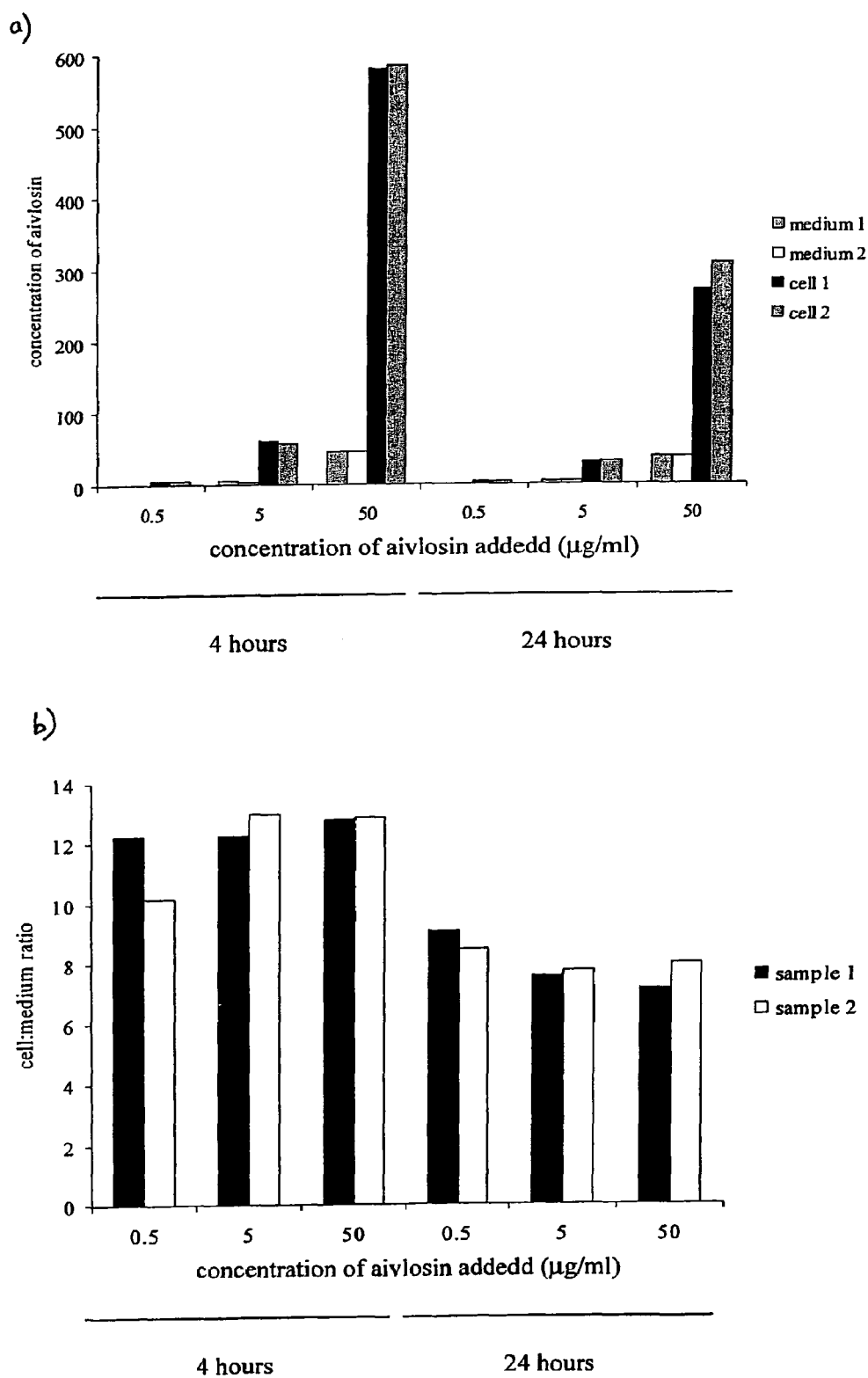

Time and Concentration Effects for Intracellular Accumulation of Tylvalosin in HRT-18 Cells Initial experiments were carried out to examine the effect of increasing concentration over time on the intracellular accumulation of tylvalosin in the epithelial gut cell line HRT-18. As seen in FIG. 5a there was a rapid (within 4 h) uptake of tylvalosin into the HRT-18 cells directly proportional to the concentration in the medium. The cells accumulated high concentrations of tylvalosin—at least 585 µg of cells. The cell:medium concentration ratio (shown in FIG. 5b) was approximately 1:12 for all three initial concentrations of tylvalosin in the medium. Similar results were obtained after 24 h incubation, however the ratios were lower.

Figure 6:
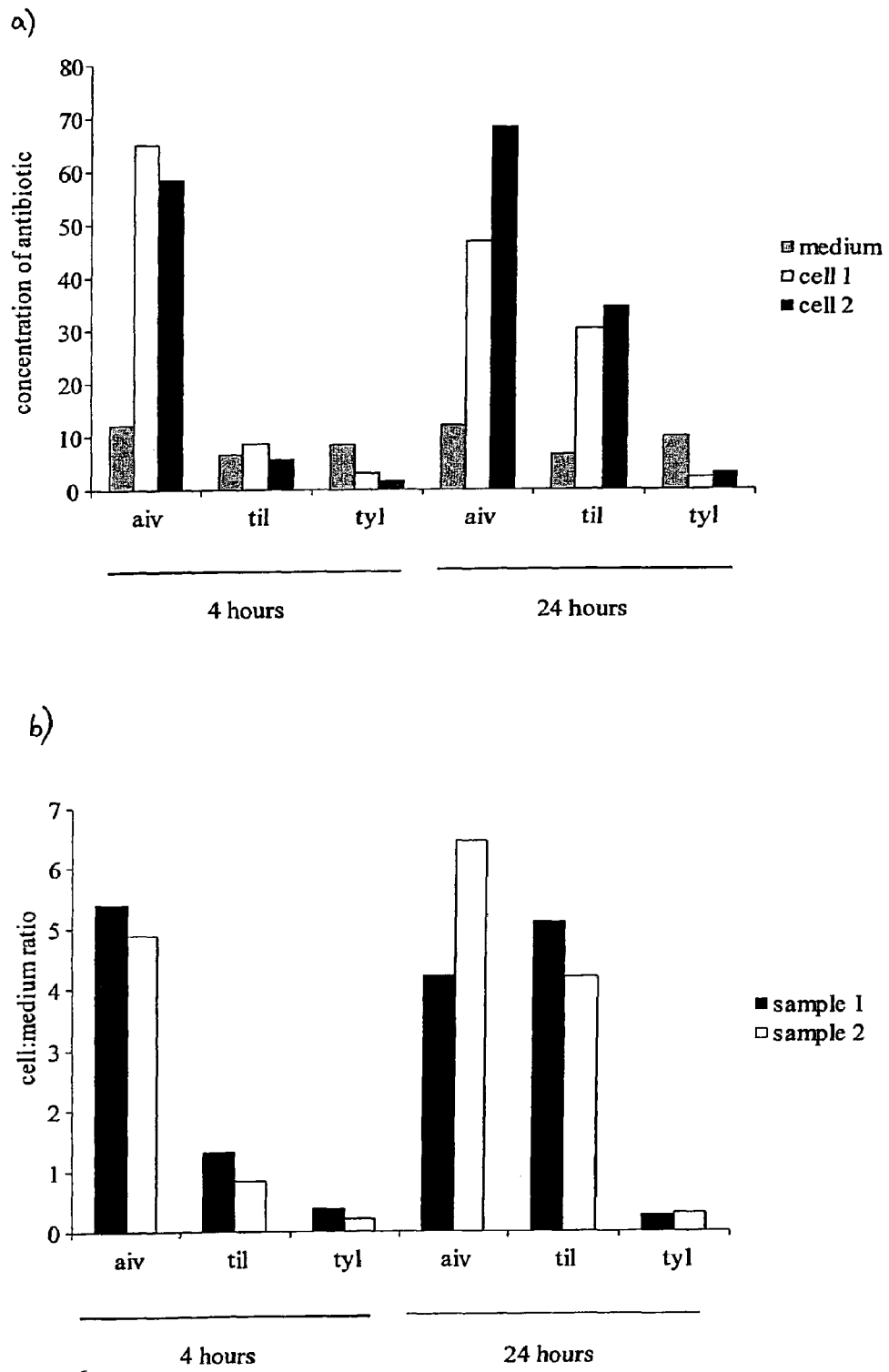

Intracellular Accumulation of Tylvalosin, Tylosin and Tilmicosin in HRT-18 Cells We then compared the intracellular accumulation of tylvalosin in HRT-18 cells with that of the related macrolides tylosin and tilmicosin. As shown in FIG. 6a tylvalosin entered HRT-18 gut epithelial cells more rapidly. An average value of 61.8 µg tylvalosin/mg cells was detected at 4 hours whilst only an average of 7.24 µg tilmicosin/mg cells was detected at the same time point.

At 24 h an average of 57.6 µg tylvalosin/mg cells was found and 32.45 µg tilmicosin/mg cells. At both time points tylosin did not readily enter HRT-18 cells. The intracellular: extracellular ratios are shown in FIG. 6b. After 4 h, tylvalosin accumulation resulted in an average value for the concentration within the cells of 5.13 fold. Only one tilmicosin sample was concentrated and this was 1.32 fold. After 24 h mean concentrations ratios were similar for tylvalosin (5.34 fold) and tilmicosin (4.64 fold). The inability of tylosin to enter HRT-18 epithelial cells meant that the concentration ratios were less than 1.

Intracellular Accumulation and Trans-Epithelial Transport of Tylvalosin in Polarised Caco-2 Cells We next examined the intracellular accumulation of tylvalosin in another gut epithelial cell line, Caco-2. These cells, when grown on permeabilised supports, can differentiate and become polarised: in that they form tight junctions between the cells and this results in the formation of an apical (upper) and basolateral (sides and lower) membrane.

Figure 7:
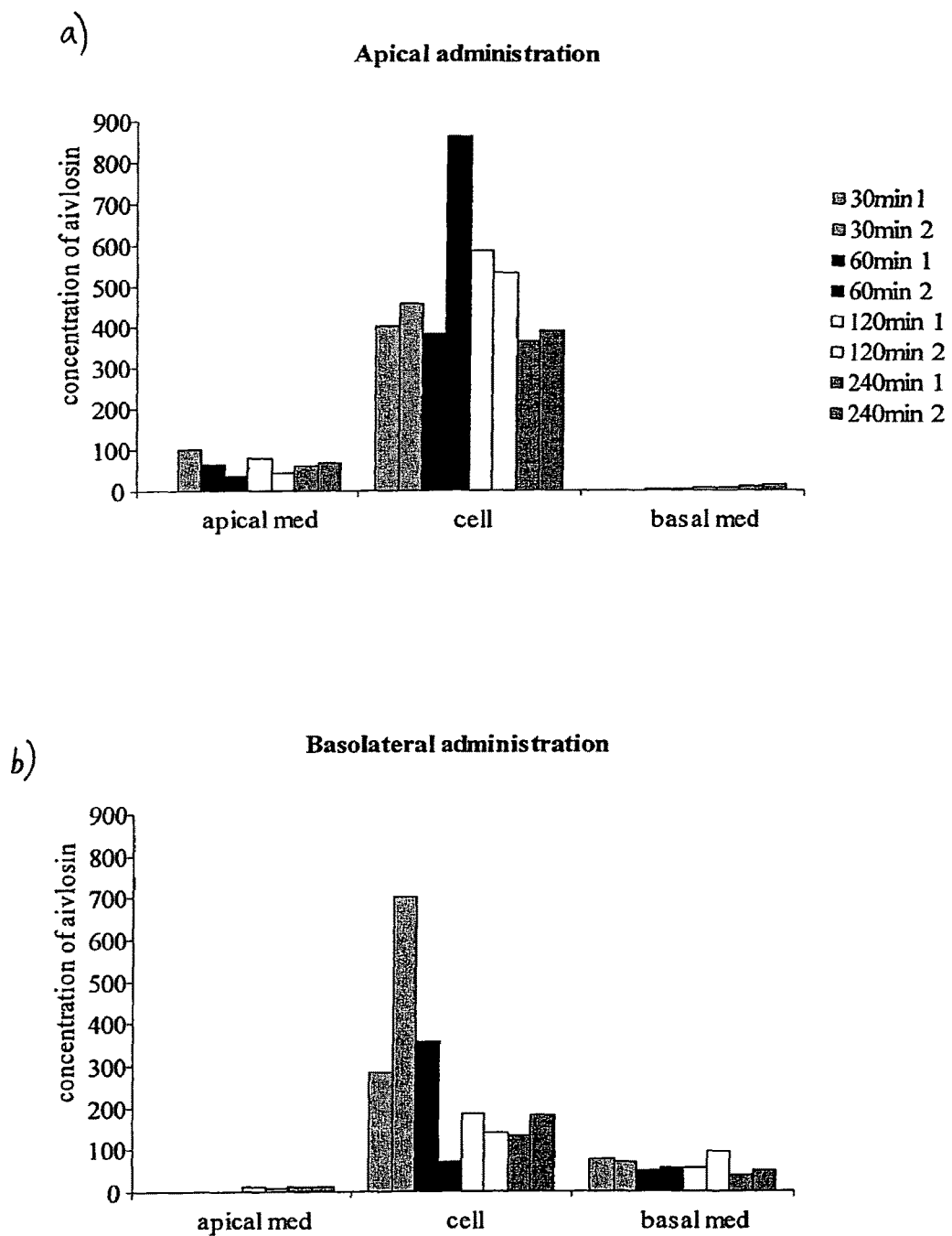
Figure 7:
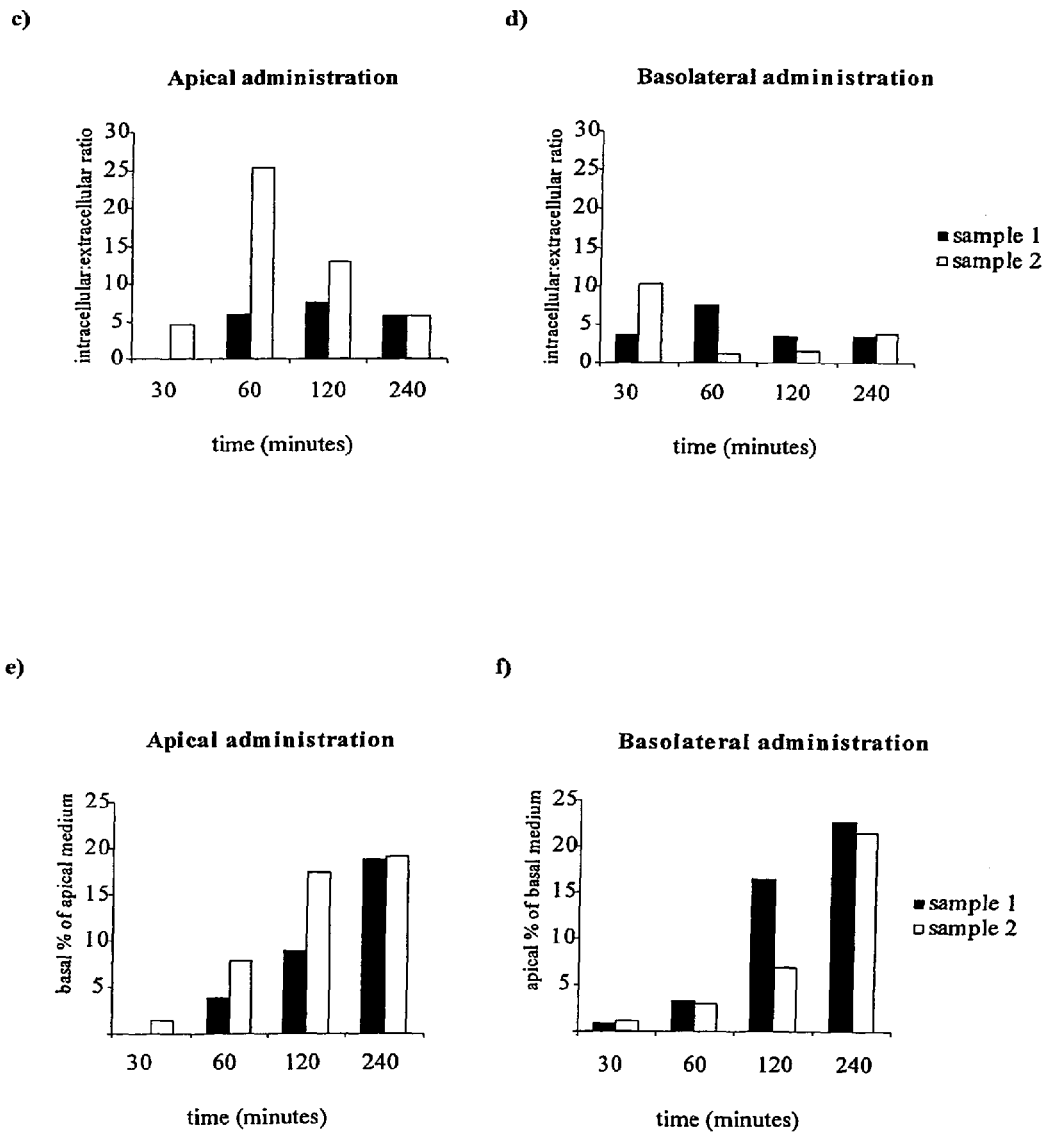

FIG. 7a shows the concentration of tylvalosin in the cells and the medium of the apical and basolateral chambers when tylvalosin was added to the medium of the apical chamber. FIG. 7b shows similar results when tylvalosin was added to the basolateral chamber. Tylvalosin demonstrates rapid entry in polarised Caco-2 cells. An average intracellular concentration of 428 µg tylvalosin/mg cells detected 30 min after apical administration (light grey bars in FIG. 7a) and 493 µg tylvalosin/mg cells after basolateral administration (light grey bars in FIG. 7b). After apical administration tylvalosin concentrations in the cells reached a maximum (559.5-620 µg tylvalosin/mg cells) between 60 min and 120 min and then decreased to 375 µg tylvalosin/mg cells at 240 min. Cells that had received tylvalosin administered in the basolateral chamber did not reach the same levels of intracellular concentration as those where it was administered in the apical chamber. The average maximum concentration reached was after 30 min incubation and after this time the intracellular concentrations decreased to 155.5 µg tylvalosin/mg cells at 240 min.

The intracellular:extracellular ratios are shown in FIGS. 7c and 7d. After apical administration (FIG. 7c) tylvalosin rapidly became concentrated within Caco-2 cells with a ratio of 4.64 after 30 min. This ratio peaked between 60 min and 120 min (average value of 10.23-15.58) and then decreased to an average value of 5.85 at 240 min. Tylvalosin also demonstrated rapid concentration after basolateral administration—an average intracellular:extracellular ratio of 7 was observed after only 30 min. After this time though the ratio decreased to 3.57 after 240 min.

We also examined the medium in the chamber opposite to the administration site (i.e. the basolateral chamber when tylvalosin was added to the apical chamber) to investigate whether tylvalosin could be transported across the polarised epithelial cells. As shown in FIGS. 7e (apical administration) and 7f (basolateral administration) similar levels of tylvalosin were detected in the opposite chamber reaching levels of 19% (FIG. 7e) or 22.05% (FIG. 7f) tylvalosin compared to the administration chamber after 240 min. The increased concentration of tylvalosin in the medium of opposite chamber coincides with the decreased levels of tylvalosin detected within the cells suggesting that the decreased intracellular concentrations may be due to the tylvalosin passing out into the medium on the opposite side of the cells.

The Intracellular Accumulation and Trans-Epithelial Transport of Tylvalosin, Tylosin and Tilmicosin in CaCo-2 Cells Similar experiments were carried out to compare the intracellular accumulation and trans-epithelial transport of tylvalosin with tylosin and tilmicosin, although we only examined the effect after apical administration. As shown in FIG. 8a tylvalosin again showed rapid entry and accumulation reaching a maximum average concentration of 42.2 µg tylvalosin/mg cells after 120 min. As before the intracellular concentration of tylvalosin decreased at the 240 min time point (to an average value of 34.3 µg tylvalosin/mg cells). Tylosin did not readily enter polarized Caco-2 cells—after 240 min only 1.86 µg tylosin/mg cells were detected. Tilmicosin demonstrated slower entry and accumulation than tylvalosin. The average intracellular concentration at 120 min was 8.6 µg tilmicosin/mg cells (compared to 42.2 µg tylvalosin/mg cells at the same time point). At 240 min tilmicosin reached an average concentration of 16.05 µg tilmicosin/mg.

Figure 8:
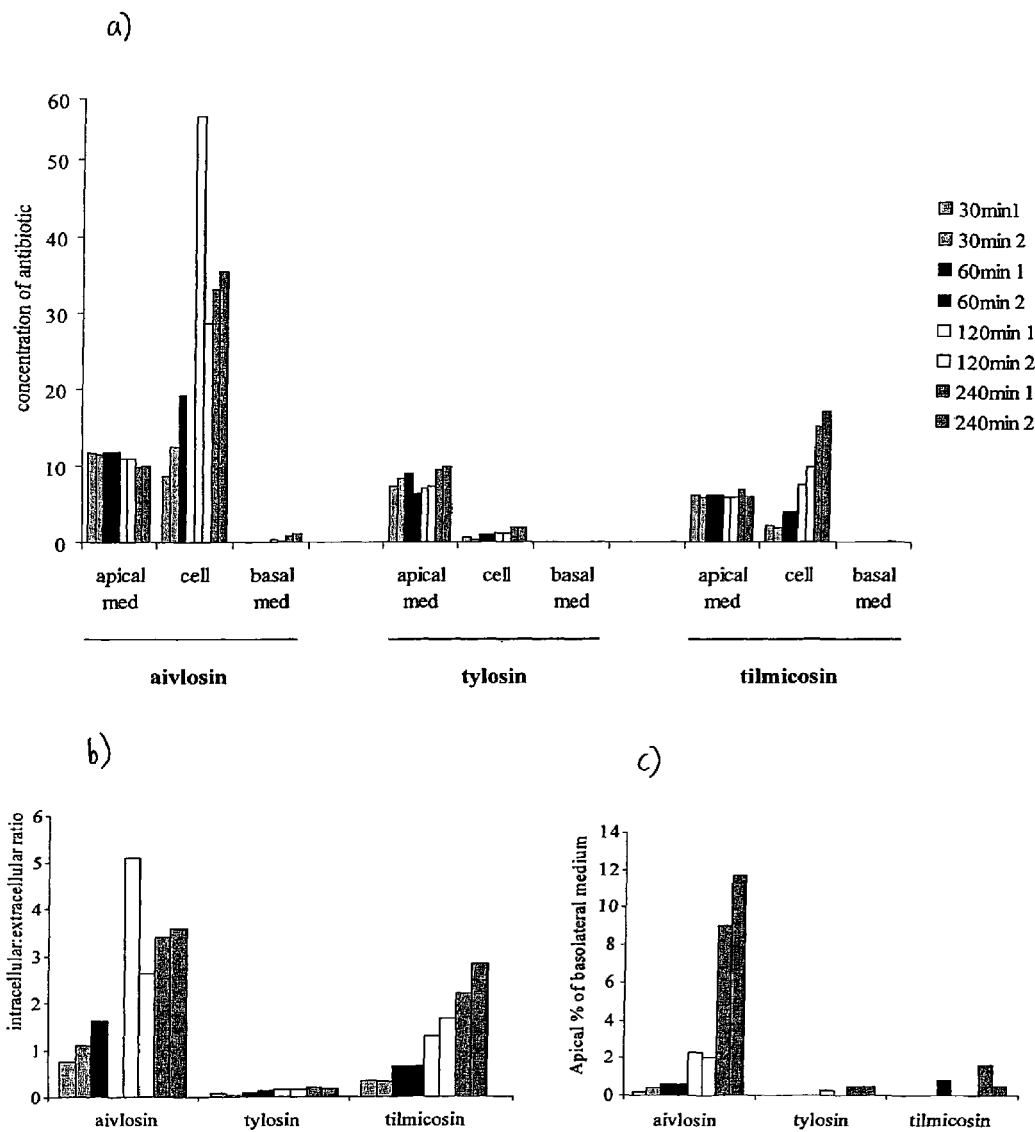

The intracellular extracellular ratios shown in FIG. 8b show that tylvalosin rapidly becomes concentrated in the polarized Caco-2 cells. Tylosin did not concentrate in these cells and tilmicosin showed an intermediate effect with slower concentration kinetics, but similar fold concentrations were reached after 240 min (3.49 fold concentration for tylvalosin and 2.5 fold concentration for tilmicosin).

The data shown in FIG. 8c indicate a more efficient transport of tylvalosin to the basolateral fluid than either tylosin or tilmicosin. After 240 min incubation with tylvalosin, the basolateral chamber contained an average of 10.47% of the apical chamber value. This compares with an average of 0.52% of the value for tylosin and 1.08% of tilmicosin.

Figure 9:
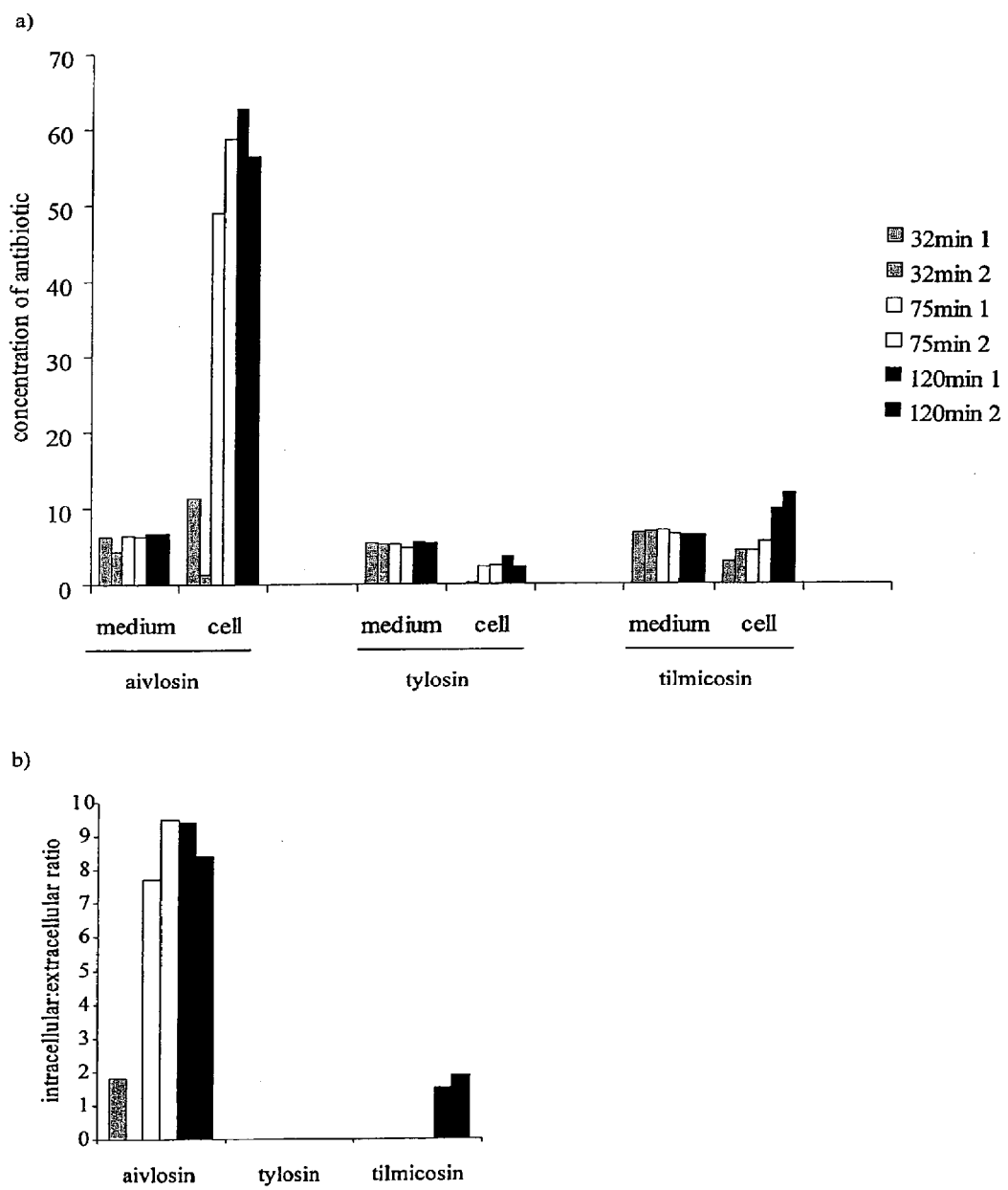

Intracellular Accumulation of Tylvalosin, Tylosin and Tilmicosin in Pig Kidney Cells The host animals typically treated with tylvalosin, tylosin and tilmicosin are swine and poultry. We examined the intracellular accumulation of these macrolides in the porcine kidney epithelial cell line LLC-PK1. As shown in FIG. 9a tylvalosin rapidly entered and accumulated in LLC-PK1 cells, after 75 min an average concentration of 53.95 µg tylvalosin/mg cells were detected compared to 2.41 µg tylosin/mg cells and 4.98 µg tilmicosin/mg cells. As shown in FIG. 9b tylvalosin reached a maximum intracellular: extracellular ratio of 8.9 at 120 min. Tylosin was not concentrated in the LLC-PK1 cells at all and tilmicosin showed 1.7 fold concentration at 120 min.

Figure 10:
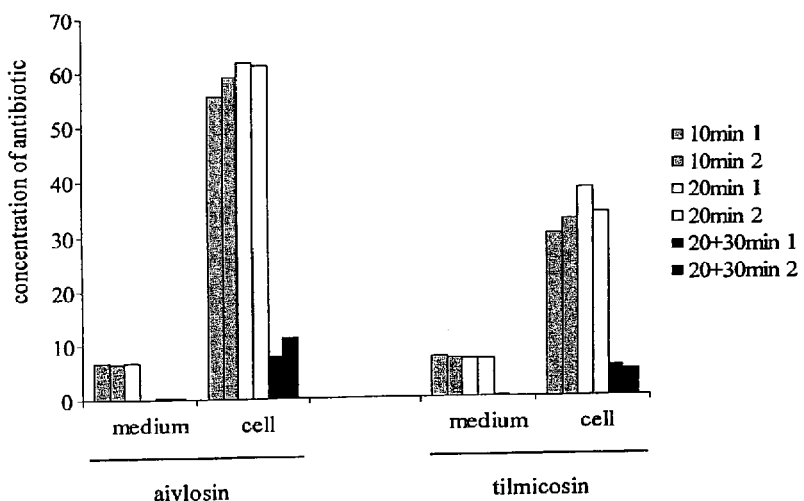
Figure 10:
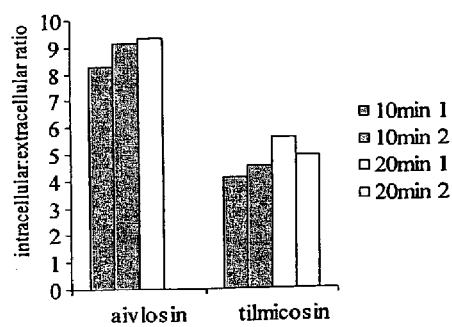
Figure 10:
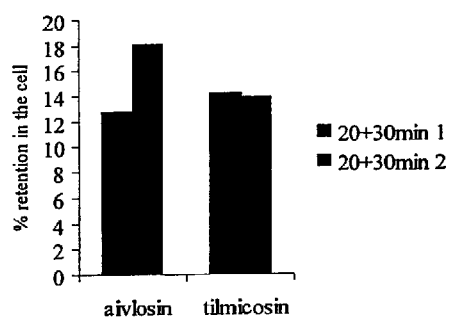
Figure 10:
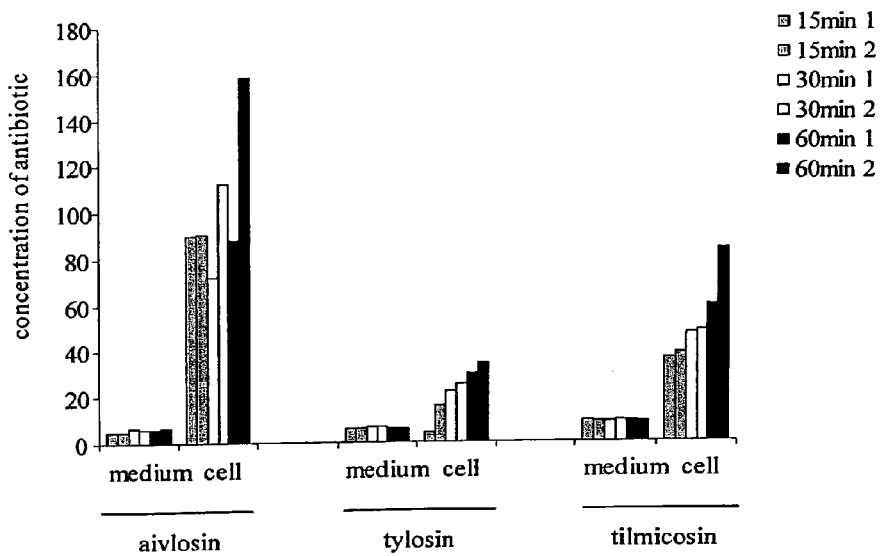
Figure 10:
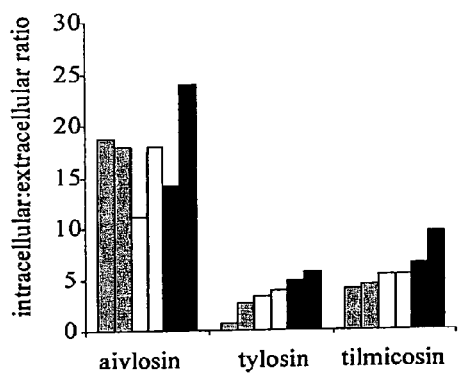

Intracellular Accumulation of Tylvalosin and Tilmicosin in Pig and Chicken White Blood Cells We also examined the intracellular accumulation of the macrolides in white blood cells isolated from chicken and swine. Tylvalosin rapidly entered pig white blood cells (FIG. 10a). After 10 min an average concentration of 57.4 μg tylvalosin/mg cells were detected compared to 31.25 μg tilmicosin/mg cells. Little increase in these values were detected at 20 min—where 61.45 μg tylvalosin/mg cells and 36 μg tilmicosin/mg cells were detected. As shown in FIG. 10b the average intracellular:extracellular ratio was 8.68 for tylvalosin, compared to 4.33 for tilmicosin. Similar ratios were found for both antibiotics after 20 min. When the cells laden with antibiotic were left in media without antibiotic, there was a transport out of the cell. The amount retained within the cell was similar for both antibiotics at about 14 to 15% (FIG. 10c). Hence, the majority of antibiotic was lost from the cells under these conditions.

The cell type equivalent of the mammalian neutrophil in chickens is the heterophil. White blood cells were isolated from chicken blood and tested for the accumulation of antibiotic. The results, as shown in FIG. 10d, demonstrate that tylvalosin rapidly accumulates within cells. At 15 min tylvalosin concentration in the cells had an average value of 89.8 μg tylvalosin/mg cells this reached a maximum value for this assay of 122.9 μg tylvalosin/mg cells after 60 min. Tylosin was able to enter these cells and showed intracellular concentrations of tylosin increasing from 10.1 μg tylosin/mg cells at 15 min to 32.1 μg tylosin/mg cells at 60 min. Tilmicosin again showed an intermediate effect and increased from 37.1 μg tilmicosin/mg cells at 15 min to 71.3 μg tilmicosin/mg cells at 60 min.

The intracellular:extracellular ratios (FIG. 10e) showed that at 15 min the intracellular concentration of tylvalosin was about 18 fold the concentration in the medium. A 19-fold concentration was detected after 60 min. Both tilmicosin and tylosin concentrated in the cells, although this varied during the experimental time period from about 4.2 to 8 fold for tilmicosin and from 2.65 to about 4.7 for tylosin.

Discussion

The uptake and accumulation of antibiotic in cells could be an important factor that could effect the replication of virus. Virus replication takes place exclusively inside cells, as the virus requires the cell's machinery for replication. Normally, antibiotics would not be expected to effect virus replication. However, in this case it has been unexpectedly found that Aivlosin® (tylvalosin) affects the replication of PRRSV and Influenza A. The comparative data for cell entry between macrolides may help explain possible differences on effects of viral replication.

In these studies the inventors have investigated the uptake and intracellular accumulation of three macrolides—tylvalosin, tylosin and tilmicosin—in human and pig epithelial cells and chicken and pig white blood cells (WBC). They demonstrated that tylvalosin was able to enter and concentrate to a greater degree than either tylosin or tilmicosin in all cells types. However the data clearly underestimated the degree of intracellular concentration because of the presence of medium between the cells (intercellular fluid) (Scorneaux and Shryock, 1999). In addition macrolides have been shown to localise within acidic cellular compartments, particularly lysosomes (Tulkens, 1991, Carbon, 1995). These compartments constitute a relatively small proportion of the cytosolic volume in epithelial cell lines and localized concentrations of antibiotic will thus be high.

Initial experiments to study tylvalosin accumulation in gut epithelial (HRT 18) cells showed that the antibiotic was concentrated efficiently to levels that depended directly on those in the medium. Further experiments comparing the uptake and concentration of tylvalosin, tylosin and tilmicosin in HRT-18 and LLC-PK1 cells demonstrated marked differences in behaviour between them. The most striking difference was that tylosin, entered both cell lines inefficiently and was not concentrated. From the HRT-18 data it might therefore be expected that the uptake into the host through gut epithelial cells is slower for tylosin than for tylvalosin. In vivo data (Okamoto et al., 1981) have shown that orally administered tylvalosin produced higher blood levels than tylosin. There is clearly a marked difference in behaviour between tylvalosin and tylosin, despite their closely related molecular structures. The observation that 3-acetyltylosin (unpublished data) and tylosin behave in the same way supports the view that the hydrophobic isovaleryl group present in tylvalosin (3-acetyl-4"-isovaleryl tylosin) is important in its efficient uptake and subsequent accumulation in acidic compartments. Tilmicosin is intermediate in terms of rate of cell entry/accumulation, but the final levels achieved are very similar to those achieved by tylvalosin. This may reflect the intermediate hydrophobicity of tilmicosin. The reported pKa values of the drugs are all consistent with protonation and accumulation in acidic compartments such as lysosomes. The failure of tylosin accumulation even over 24 hours probably reflects its limited ability to cross both the plasma membrane and intracellular organelle membranes.

Investigation of the uptake and excretion of macrolide antibiotics using Caco-2 cells extended the HRT-18 cell work. Caco-2 cells are human colon adenocarcinoma cells. They are epithelial cells that exhibit the characteristics of mature enterocytes including microvilli, tight junctions, enzymes such as small intestine hydrolases, nutrient transporters and membrane proteins such as CTFR, ICAM-1, interleukin-1 receptor, interleukin-6 receptor and alpha1 antitrypsin receptor (Varilek et al., 1994, Kaiserlian et al., 1991, Zweibaum et al., 1983, Sood et al., 1992, Molmenti et al., 1993). These features make them well suited to evaluate the ability of drugs to pass through epithelia in a directional manner.

Polarised cells have been used in numerous studies to examine the entry routes and transport of several different types of molecules, including immunoglobulins and albumins (Ellinger et al., 2001, Maples et al. 1997, Antohe et al., 1997). These cells have also been used to study the polarised entry and release of viruses (Cordo et al., 2005, Chu and Ng 2002, Rossen et al., 2001, Jarvis et al., 1999).

The results from Caco-2 cells in the present investigation demonstrate a rapid concentration of tylvalosin at 30 min (the first time point used) for both apical and basolateral administration. Similar values were obtained using either route of administration, suggesting similar mechanisms of uptake at both surfaces. Tylvalosin moved across the cell to the opposite surface and was released into the medium. Thus antibiotic administered at the apical surface could be detected in the basal medium. This effect increased over time, so that after 4 h about 20% of the total amount of tylvalosin had been transported. This appears to be an efficient process, taking into account the small number of cells involved in the transport. The movement of tylvalosin is down a concentration gradient. The mechanism by which this occurs is unknown. Tylosin was not concentrated intracellularly in Caco-2 cells, tilmicosin showed intermediate behaviour—rapid entry did not take place but over time the antibiotic was concentrated intracellularly and a modest amount was transported across the epithelium. This in vitro work using gut epithelial cells suggests that in vivo antibiotic could be transported from the lumen of the gut into the body and also from the body into the gut lumen. This has been shown for the macrolides clarithromycin and azithromycin. Nightingale (1997) reported that azithromycin is eliminated by the hepatic route with some biliary excretion, and is also eliminated directly, by secretion into the lumen of the intestine. This transintestinal route is believed to account for the elimination of 30 to 35% of the total administered dose. The same author stated that clarithromycin, undergoes both hepatic and renal elimination and in addition, transintestinal elimination, which accounts for excretion of about 10% of the total dose of this macrolide.

Previous studies have highlighted the increased uptake and greater accumulation of macrolides by neutrophils and cells of the monocyte/macrophage lineage. Our data demonstrated that tylvalosin rapidly entered and accumulated in both chicken and pig white blood cells after only 10 min incubation. The uptake was greater than that seen for either tylosin or tilmicosin. A major function of neutrophils is to phagocytose pathogenic organisms. Cells laden with antibiotic may be better able to rid the host of susceptible organisms by increasing the kill capacity within the cell. Also, by releasing antibiotic into the immediately surrounding medium, the cells enable high concentrations of antibiotic to be produced locally, which allows extracellular killing to take place. In the present study our technique allowed the comparison of the uptake of tylvalosin and tilmicosin in pig WBCs. Tylvalosin was rapidly taken up by pig white blood cells (the majority of which are neutrophils) and after just 10 min incubation an IC:EC ratio of 9 was obtained. Tilmicosin also rapidly entered the porcine WBCs, although the concentration attained was less (×4). When avian WBCs were used, tylvalosin reached high IC:EC ratios, about ×18, within 15 min, which were maintained. Both tylosin and tilmicosin were also concentrated, but to a lesser extent. Macrolides have been shown to have effects on the innate immune system, which include reducing inflammation by causing increased apoptosis of neutrophils (Chin et al., 1998) and reducing the recruitment of neutrophils to the site of infection (Ianaro et al, 2000). These effects could also assist the host in preventing the pathology that can be associated with inflammation.

There are several different mechanisms by which a molecule may enter cells. These include passive diffusion (for lipid-soluble molecules) down a concentration gradient, active transport and endocytosis in its various forms (clathrin-mediated, caveolae-mediated, pinocytosis, macropinocytosis and phagocytosis as described by Pelkmans and Helenius 2003, Stuart and Ezekowitz 2005). The movement of macrolide antibiotics into cells has been studied but the information is rather scant. Many of the studies fail to distinguish between the process of crossing the plasma membrane into the cytosol and the process of accumulation in acidified vesicles. It is likely that entry into the cytosol is a passive, concentration gradient-dependent process. The uptake of macrolides has been shown to be greater at alkaline pH. This confirms the view that passive diffusion of uncharged molecules is favoured. Accumulation of macrolides does not take place at 4° C.; this is possibly because the proton pumps that acidify endosomes and lysosomes are not active at this temperature rather than that an active process at the plasma membrane is inhibited, but the observation that azithromycin is still concentrated in cells pretreated with metabolic inhibitors (Gladue and Snider, 1990) suggests that a pre-existing pH gradient should be sufficient to allow macrolide accumulation in endosomes and lysosomes. The effect of low temperature may thus be due to a dissipation of the low pH in these organelles or, more probably, to a reorganisation of plasma membrane structure that slows diffusion more dramatically than would be predicted from the normal effect of temperature on diffusion rates. The ability of molecules to cross membranes in the absence of specific channels or transporters is strongly dependent cm their ability to "dissolve" in the lipid phase of the membrane. Hydrophobicity is thus likely to be the key determinant of the efficiency of macrolide entry and accumulation, with pKa values also playing a role in some cases. The properties of tylvalosin reported in this publication are consistent with its possession of an isovaleryl group and a pKa of 7.6.

The issues surrounding the relationship between antibacterial activity and efficient cellular accumulation are complex. Carbon (1995) stated that it is very difficult to predict, for a given type of cell and a given type of intracellular infection, the actual intracellular concentrations which are necessary for an antimicrobial drug to be effective in vivo. A key consideration is, however, the spatial relationship between the bacterium and the cell accumulating the antibiotic. Three types of interaction are of particular interest in the context of macrolides such as tylvalosin, tylosin and tilmicosin. The first involves those intracellular bacteria, which are capable of survival in the low pH environment of the endosome/phagolysosome. In this case accumulation of the drug in the acidic compartment should make them highly effective. The second type of interaction involves escape from a vesicle into the cytosol. In this case the accumulation of antibiotic in the vesicle will only be of relevance prior to the bacterium's escape, but the vesicle-accumulated material may provide a reservoir of antibiotic for release into the cytosol. The third form of interaction involves close extracellular interaction in which the bacterium typically binds to the plasma membrane of the "host" cell. In this case also, accumulation will be of relevance only if the cell acts as a reservoir of drug that is slowly released into the surrounding milieu. The properties of tylvalosin described in this paper are consistent with efficacy against bacteria that enter into any of these types of relationships with cells.

The difficulty in extrapolating from in vitro properties is illustrated by experiences with other efficiently accumulated, relatively hydrophobic macrolides. Thus the cellular uptake of azithromicin is relatively high, with uptake slower than that for other macrolides, but this is not paralleled by an increase in efficacy (Labro, 1996). Similarly, high intracellular to extracellular ratios have been reported for tilmicosin (Scorneaux and Shryock, 1998a,b, 1999) but the efficacy is not exceptional, especially at the commercial dosage used, as demonstrated by Reeve-Johnson et al., (1997a,b) for mycoplasmosis in chickens. This antibiotic, that is found in high intracellular concentrations and that moves across the cell membrane relatively easily, might have been expected to be highly effective against, for example, mycoplasma. It remains to be determined what features of the 3' acetyl4'isovaleryltylosin molecule account for its particular efficacy against a range of important cell-associated pathogens.

Our results using epithelial cells from the pig (PK) gave similar results to those using human (HRT-18, Caco-2). In fact the results were very clear-cut and once again tylvalosin was rapidly concentrated in the cells, whereas tylosin was not concentrated and tilmicosin had intermediate properties.

Thus, the data presented in this study indicate marked differences in the cellular uptake of the macrolide molecules, even though tilmicosin is derived from fraction B of tylosin and tylvalosin is derived from fraction A. 3' acetyl4'isovaleryltylosin differs from 3' acetyltylosin (3AT) because it has the isovaleryl group. The ability of tylvalosin to rapidly penetrate cells appears to be due to the isovaleryl group, which is shown in the data from this study and also from a previous study (Tsuchiya et al., 1981) that suggested that tylvalosin is more lipophilic than either tylosin or 3AT. 3AT is a major metabolite of tylvalosin, and is generated within the cell. Presumably, the metabolite has reduced ability to exit the cell, compared to tylvalosin. The fact that 3AT is still metabolically active and is likely to remain in the cell longer than the parent molecule might be advantageous clinically.

Example 4

Figure 11:
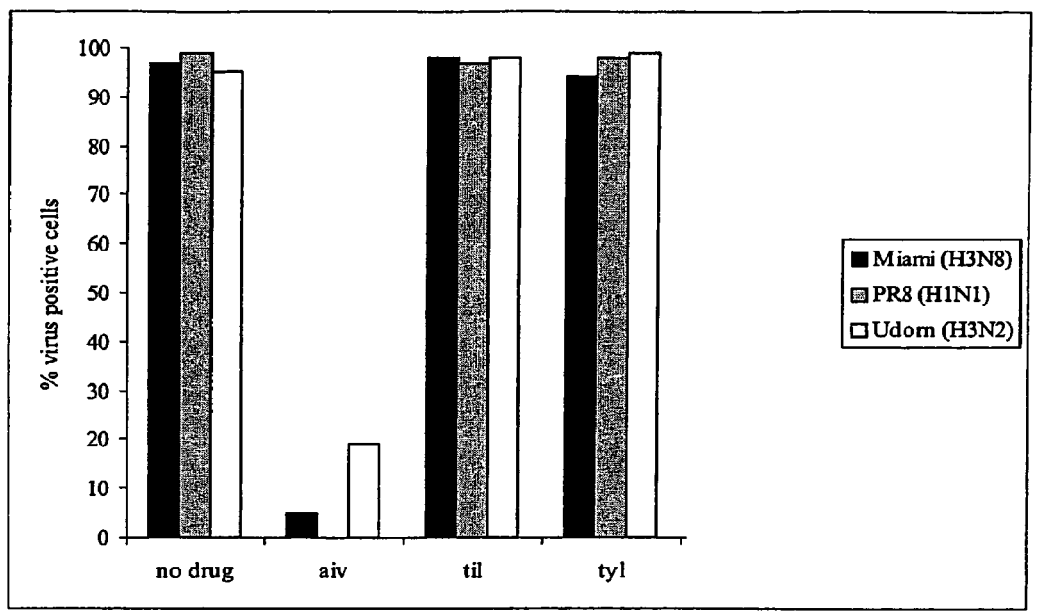
FIG. 11 shows the effect of Aivlosin® (tylvalosin), tilmicosin and tylosin an influenza virus infection of MDCK cells.

Further to example 1, experiments to examine the effect of tylvalosin on the infection of MDCK cells by equine influenza strain Miami (compared to human PR8 and Udorn strains) were carried out. MDCK cells were pretreated with 1 µg/ml tylvalosin, tylosin, or tilmicosin for 4 hours. Cells were then infected with PR8, Udorn or Miami (at a multiplicity of infection of 10) in the presence of the drugs. Cells were fixed 4 hours post infection and infection was assessed by indirect immunofluorescence to influenza nucleoprotein. The results are shown in FIG. 11.

Tylvalosin (at 1 µg/ml) inhibited infection of MDCK cells by equine influenza strain Miami by 92%, Udorn by 76% and completely inhibited PR8 infection.

Example 5

Experiments were carried out to examine the effect of tylvalosin, tylosin, and tilmicosin on PRRSV infection and cell spread after infection at low multiplicity and also the effect of adding the drugs after infection.

Figure 12:
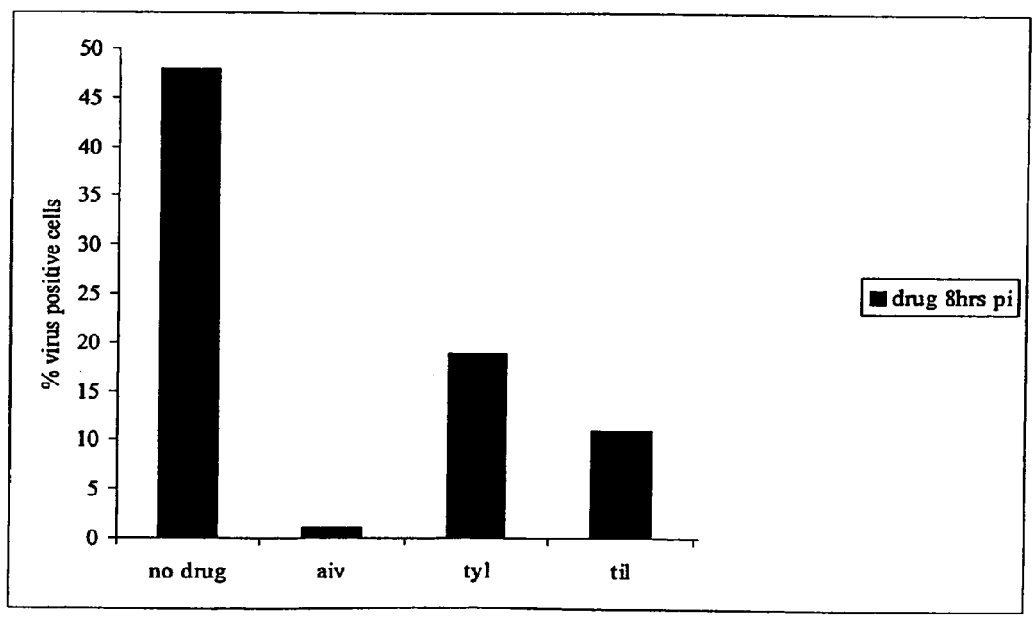
FIG. 12 shows the effects of Aivlosin® (tylvalosin), on PRRSV spread after infection.

MA104 cells were infected with PRRSV at moi of 0.01 (should infect roughly 10% of the cells in the first round). 8 hours post infection tylvalosin, tylosin and tilmicosin were added at 1 µg/ml. Cells were harvested 28 hours post infection and infection was assessed by indirect immunofluorescence. The results showing the number of virus positive cells for each treatment are shown in FIG. 12.

As stated above a moi of 0.01 should infect roughly 10% of the cells. However, after 28 hours the virus will have completed one round of infection and will have infected neighbouring cells. We have found that viral antigens can be detected 10 hours post infection at low levels. This detection increases 16-20 hours post infection and by 24 hours low levels of expression in neighbouring cells can be detected.

The addition of drugs 8 hours post infection should have no effect on the primary infection (i.e. no effect on entry of input virus). It could, however, effect viral replication directly or indirectly through other mechanisms and could also effect virus entry during the secondary round of infection where virus produced by the initially infected cells infects neighbouring cells.

The addition of Aivlosin® (tylvalosin) 8 hours post infection inhibited PRRSV infection reducing infection to 1% virus positive cells. Aivlosin® (tylvalosin) appeared to inhibit virus replication (fewer infected cells were detected), prevented spread of the virus to neighbouring cells and also reduced the bystander effect seen in untreated/infected cells, where neighbouring cells not showing viral antigen expression round up.

Example 6

Experiments were carried out to determine whether tylvalosin has an effect on equine arteritis virus (EAV). The inventors found that EAV infection was not blocked by Tylvalosin or by nocodazole, suggesting that EAV does not traffic to late endosomes.

Example 7

Studies to Examine the Effect of Known Inhibitors of PRRSV Infection when Added at Various Times Pre and Post Infection When added 4 hours before infection chlorpromazine, chloroquine, nocodazole, cytochalasin D and Aiviosin® (tylvalosin) inhibited initial PRRSV infection and thus no spread is observed. When added at the time of infection chlorpromazine, chloroquine, cytochalasin D and tylvalosin inhibited initial PRRSV infection and thus no spread is observed. Nocodazole did not inhibit initial infection. Nocodazole treated cells did still produce the long processes indicating that their generation is not dependent upon microtubules even though they contain them.

When added either 2 or 4 hours after infection only Aivlosin® (tylvalosin) inhibited infection of the initial site of infection and the spread. Chlorpromazine treated cells showed the initial site of infection but the drug appeared to prevent spread. Nocodazole had no effect on infection (due to toxicity its effect on spread is unclear again) and again the long processes containing virus were observed. Cytochalasin D had no effect on the initial infection as infected cells were detected, however the long processes were absent and no spread could be detected. This suggests that the processes are driven by actin polymerisation and that they are required for spread of the virus from the initial site of infection. Chloroquine had no effect on initial infection or virus spread when added post infection.

Figure 13:
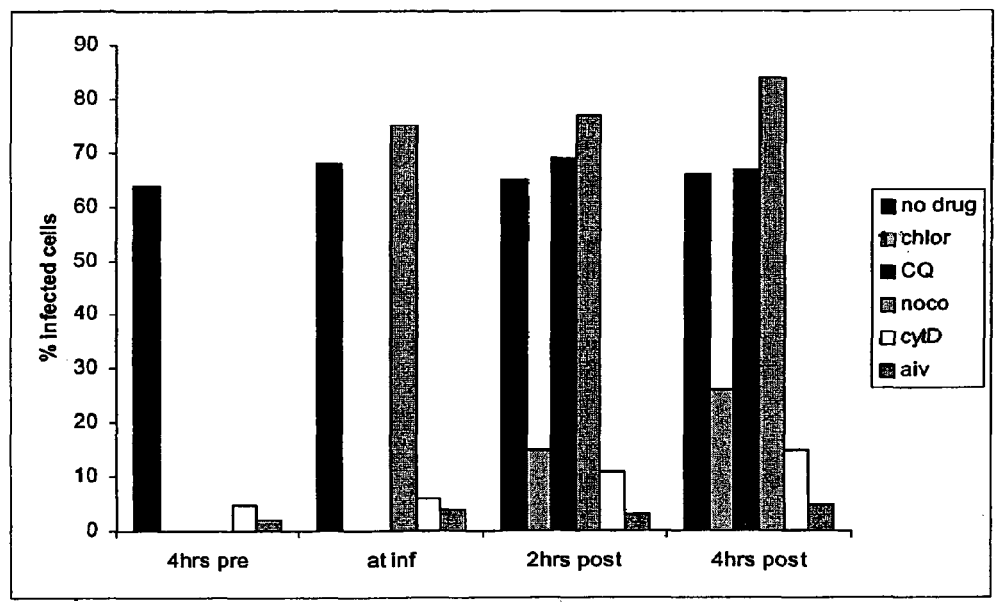
FIG. 13 shows the effect of various chemicals (chlorpromazine, chloroquine, cytochalasin D, nocodazole) and Aivlosin® (tylvalosin), on PRRSV.

The results are shown in FIG. 13.

Example 8

Comparison of the Sensitivity of PRRSV, EAV and FCV to Chloroquine

Figure 14:
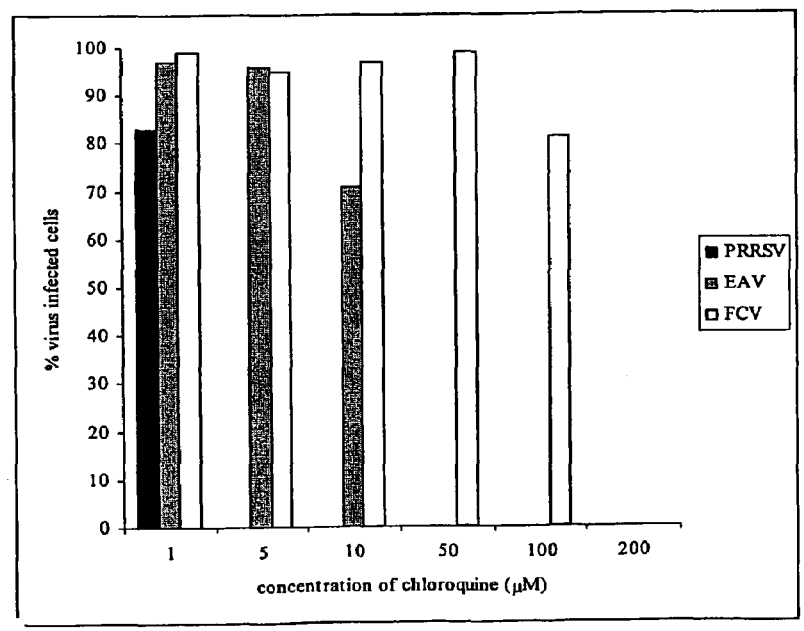
FIG. 14 shows the effect of various doses of chloroquine on the replication of PRRSV, EAV (equine arteritis virus) and FCV (feline calicivirus).

Feline calicivirus, equine arteritis virus and PRRSV all require endosomal acidification for successful infection of their host cells. Raising the endosomal pH with drugs such as chloroquine has demonstrated this. Chloroquine is a weak base and raises the endosomal pH by sequestering protons (i.e. greater concentrations of CQ will sequester more protons and raise the pH higher). The effect of increasing concentrations of CQ are shown in FIG. 14. The data show that relatively low concentrations of CQ (less than 5 µM) are required to inhibit PRRSV infection suggesting that even a modest elevation in endosomal pH is sufficient to inhibit virus entry Inhibition of FCV requires high concentrations of CQ (200 µM and above) and EAV is inhibited by 50 µM and above. The higher concentrations of CQ suggest that increased pH elevation is required to inhibit FCV and EAV. These data all indicate that PRRSV requires passage through endosomes with much lower pH (i.e. in late endosomes) than either EAV or FCV (i.e. in early endosomes).

Example 9

US Strain of PRRSV

Figure 16:
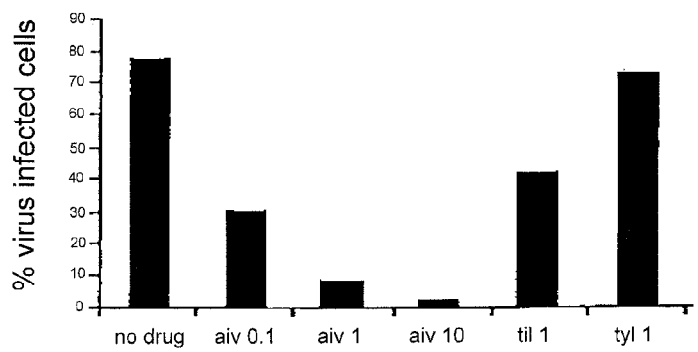
FIG. 16 shows the effect of various macrolides on the replication of VR2332 (an American type 1 PRRSV strain).

The inventors also infected MA104 cells with VR2332 (a US strain of PRRSV) to examine the effect of tylvalosin on the infection. The results are shown in FIG. 16.

2MA104 cells were pre-incubated with Aivlosin®, tylvalosin, tylosin, or tilmicosin at the concentrations shown for 4 hours. Cells were then infected with VR2332 at moi of 10 in the presence of drugs. Cells were then incubated for 20 hours. Infection was assessed by indirect immunofluorescence.

The results are comparable with those seen for the European strain examined previously.

Example 10

VR2332 (US Strain of PRRSV) Entry Assay

MA104 cells were pre-treated with chlorpromazine, chloroquine, nocodazole or cytochalasin D for 30 minutes; or tylvalosin, tylosin or tilmicosin for 4 hours. Cells were then infected with VR2332 at moi 10 and incubated overnight.

Figure 17:
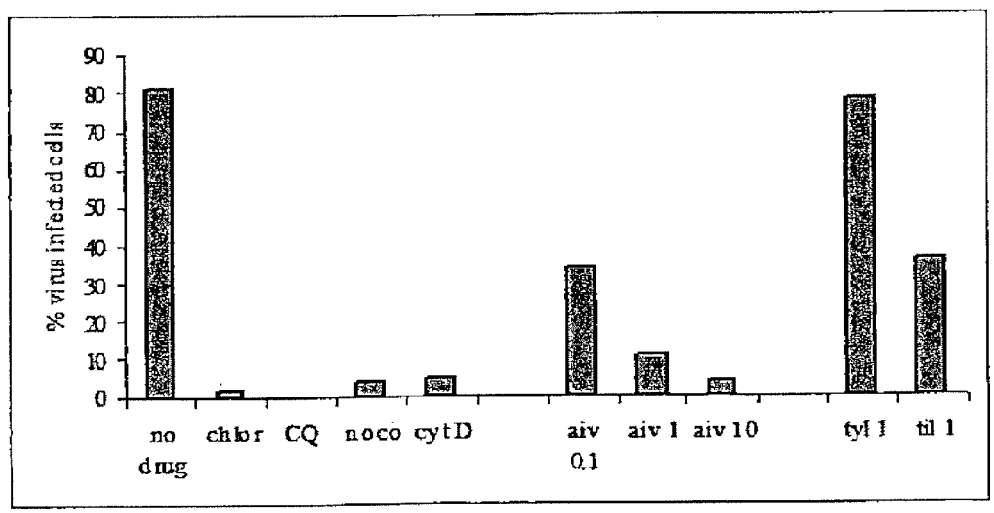
FIG. 17 shows the results of an assay for the entry of VR2332.

The results shown in FIG. 17 show that the US strain of PRRSV is also sensitive to tylvalosin but not tylosin. Tilmicosin shows partial inhibition at the concentration used.

Example 11

Effect of Tylvalosin on Virus Infection of HeLa or HT29 Cells: Virus at High and Low Multiplicity Work has shown that tylvalosin treated HeLa cells are highly resistant to virus infection. The inventors have repeated this assay with a number of viruses and compared this with virus infection of HT29 cells (a cell line routinely used for enterovirus infection). Virus was added at high multiplicity (to look at entry) and low multiplicity (to look at virus spread in the cell mon player).

Cells were treated with tylvalosin, tylosin, tilmicosin and chloroquine for 4 hours. Cells were then infected with virus at moi 10 for 4 hours or moi 0.1 for 16 hours.

Tylvalosin inhibited influenza virus entry and coxsackie B5 virus entry. Chloroquine also inhibited entry of all three viruses. Tylosin and tilmicosin had no effect. EV11 was unaffected by any of the treatments.

Figure 18:
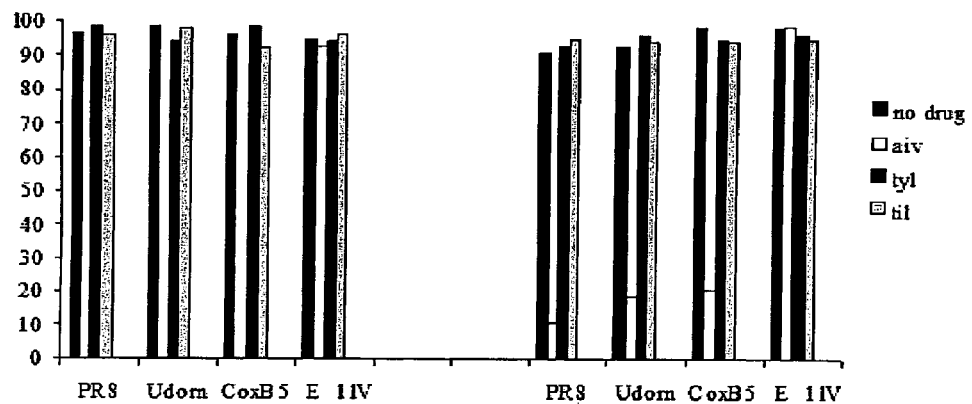
FIG. 18 shows the effect of tylvalosin on virus infection of HeLa and HT29 cells.

Tylvalosin and chloroquine inhibited influenza virus and coxsackie B5 virus infection at low multiplicity. Tylosin and tilmicosin had no effect. Surprisingly EV11 was inhibited by tylvalosin in the low multiplicity assay. Tylvalosin appeared to be inhibiting virus spread as initial sites of infection could be seen by immunofluorescence, but no secondary sites could be seen. The results are shown in FIG. 18.

Example 12

Influenza Virus Time Course

MDCK cells were grown in 24 plates with or without coverslips (cells grown on coverslips are used in immunofluorescence assays). Cells were treated with tylvalosin at 1 µg/ml for 4 hours. Cells were then infected with Udorn (moi 0.1).

Samples were harvested at 4, 8, 16 and 24 hours.

Figure 15A:
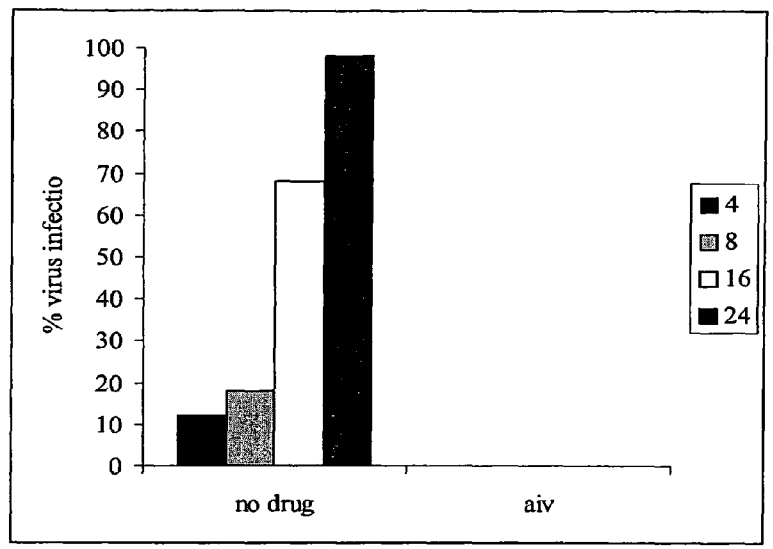
FIG. 15 shows the effects of Aivlosin® (tylvalosin) on Influenza virus (strain Udorn)
  a) percentage of virus infected cells in cell monolayer
  b) plaque assay used to quantify the viral titre in cells pre-treated with Aivlosin® (tylvalosin) or not treated. Replication of PRRSV virus is inhibited in treated cell monlayers, only residual viral inoculum being detected.
Figure 15B:
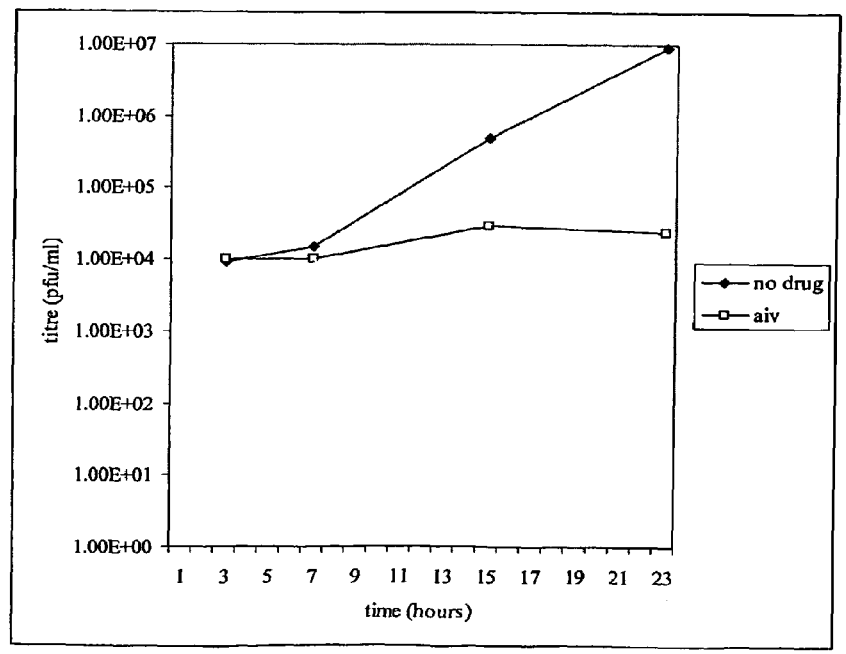

FIG. 15a shows the results of the immunofluorescence assay and 15b the plaque assay.

In both assays, Aivlosin® (tylvalosin) inhibited influenza strain Udorn infection over the 24 hour period of the assay.

Example 13

Acidine Orange Assays

Figure 19:
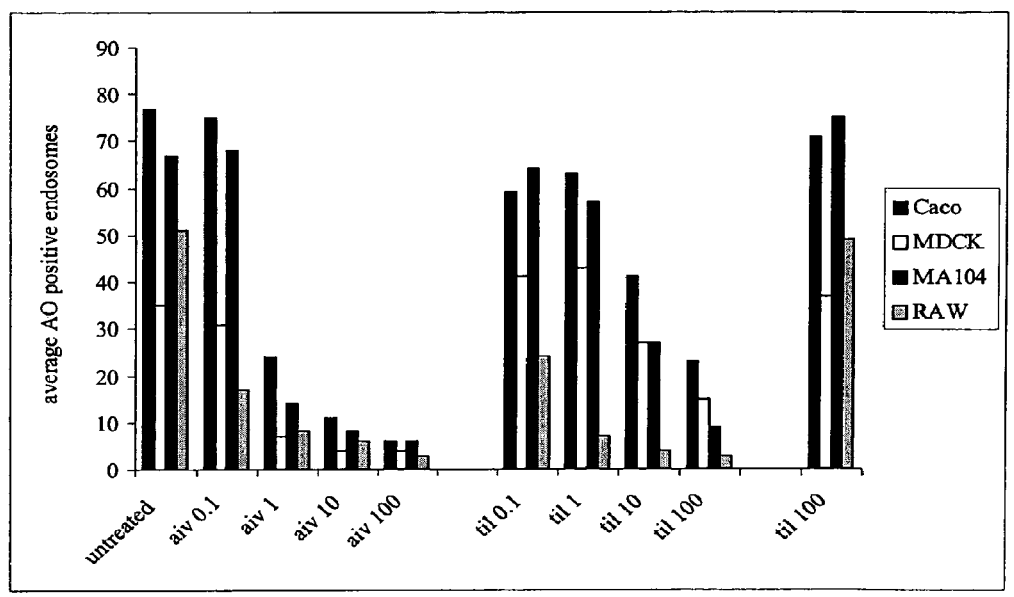
FIG. 19 shows the results of an acridine orange assay to test the effect of tylvalosin on endosomal pH.

Acridine orange is a dye that causes cells to fluoresce green with the exception of acidic compartments (such as endosomes) that appear red—due to the protonation of the dye and quenching of the green fluorescence. A substance that raises the endosomal pH will prevent the appearance of the red fluorescence. The effect of Aivlosin® and other macrolide antibiotics on a the staining of endosomes by acridine orange in number of cells lines was determined (see FIG. 19). An area of cells grown on a glass coverslip is first selected using a DAPI stain. This stain shows the nucleus of the cell as blue. This selection procedure helps reduce any bias in the results. The green and red filters on the epifluorescence microscope were then used to examine about 20 cells. The number of red spots (endosome vesicles) in was determined. The average number of Acridine orange stained endosomes was counted.

Tylosin did not have much effect on raising the pH in the endosomes of any cell line. Aivlosin® (tylvalosin) and tilmicosin had similar effects in RAW cells. However, Aivlosin® (tylvalosin) had greater effects than tilmicosin in epithelial cells.

These results show that Aivlosin® (tylvalosin) raises the pH in endosomes. PRRSV requires acidic conditions for fusion and entry into the cell cytoplasm. A rise in pH could prevent this fusion process and subsequent virus entry and propagation in the cell.

Example 14

Determination of Efficacy of Tylvalosin for the Control of PRRSV

Materials and Methods
Experimental Design
All study procedures and animal care were approved by and in accordance with the guidelines of the Iowa State University Institutional Committee on Animal Care and Use.

Sixty-eight, 10- to 12-day-old crossbred barrows were procured from a herd seronegative and not vaccinated for PRRSV or *Mycoplasma hyopneumoniae*, as designated by the principal investigator. All pigs were tagged and weighed upon arrival. The pigs were assigned to 4 groups of 16 pigs each (Table 1). Allocation of pigs to groups was performed by a statistician,—The pigs were assigned to group using block (by weight) randomization so that the groups would be balanced on pig weight. Each group was house in separate, but identical rooms in the isolation facilities. Feeders and nipple waterers were present in each deck so pigs could eat and drink ad libitum throughout the trial. The four extra pigs were terminated prior to Trial day 0 and were not included in the trial.

Each treatment group consisted of 2 pens with 8 pigs each. Upon arrival, the pigs received a commercial, concentrated medicated diet free of any known contaminates or pesticides and containing 50 grams per ton Mecadox (Philbro Animal Health). All pigs were treated with ceftiofur hydrochloride (Excenel®, Pfizer Inc.) according to label directions for 3 days following arrival.

Production Parameters
Pigs were weighed individually upon arrival and on Trial Days 0, 7, 14, 17, and 28 to evaluate weight gain (average daily gain).

Clinical Evaluation
Pigs were assessed daily for 10 days for clinical respiratory signs including cough and increased respiratory rates as previously described[1]. Scoring was: 0=normal, 1=mild dyspnea and/or tachypnea when stressed; 2=mild dyspnea and/or tachypnea when at rest; 3=moderate dyspnea and/or tachypnea when stressed; 4=moderate dyspnea and/or tachypnea at rest; 5=severe dyspnea and/or tachypnea when stressed; and 6=severe dyspnea and/or tachypnea when at rest. In addition, any coughing observed was recorded as 0=no coughing and 1=coughing. Either a veterinarian or a qualified individual made the observations.

Treatment

Three groups of pigs received medicated feed containing Tylvalosin at 3 different concentrations provided by ECO Animal Health.—Pigs in the three groups received the medicated diet the entire duration of the trial from Trial Day 0 until Trial Day 28. The fourth group was fed identical, non-medicated feed.

Feed Assays

Representative one-pound samples of the feed were collected on Trial Day 17 and 28. Feed samples were not collected at the initiation of the trial. All samples were marked with the code number, sampling site, protocol number, date of sampling and signature and placed in a plastic freezer bag. The size was approximately 0.5 kg of feed. Duplicate samples were collected. One set of samples was sent on dry ice to ECO Animal Health to be assayed by the analytical laboratory and the duplicate sample retained on the site.

Challenge Procedure

An inoculating dose of $1 \times 10^5$ tissue culture infectious dose $(TCID)_{50}$ in 2 ml of media of a high virulent PRRSV strain, VR2385, was administered intranasally to all pigs.

Necropsy

Six pigs from each treatment group were necropsied on Trial Day 17 (10 days post infection) and the remaining pigs were necropsied Trial Day 28 (21 days post infection). On Trial Day 17, two randomly selected pigs from each pen were necropsied and the remaining pigs (n=10) necropsied on Trial Day 28. Pigs were administered an AVMA approved euthanasia solution (Fatal-Plus, Vortech Pharmaceuticals, Dearborn, Mich.) followed by exsanguination. The trachea and lungs were clamped with a forceps and removed from the pig. The lungs were evaluated for macroscopic lesions consistent with PRRSV as previously described. Tracheal swabs were collected aseptically for bacterial isolation using standard microbiological methods. The lungs were lavaged with 50 ml phosphate buffered saline (PBS) containing antibiotics (9 µg of gentamicin/ml, 100 U penicillin/ml and 100 µg streptomycin/ml).

A portion of each lung lobe was collected and processed for histopathological examination. Histopathologic lesions were scored as previously described. Briefly, 0=no microscopic lesions, 2=moderate multifocal interstitial pneumonia, 3=moderate diffuse interstitial pneumonia and 4=severe interstitial pneumonia. Immunoshistochemistry was scored as previously described. Briefly, 0=no PRRSV antigen positive cells, 1=1-10 positive cells/field, 2=11-30 positive cells/field, 3=31-100 positive cells/field and 4=>100 positive cells/field.

Real-Time PCR

Blood for PCR was collected on Trial days 0, 10, 17, 21 and 28.

Total RNA was extracted using the QIAamp Viral RNA Mini kit (QIAGEN) according to the manufacturer's instruction, and solubilized in 60 µl of elution solution. The RNA extracts were stored at −80° C. until real-time RT-PCR amplification was carried out.

The forward primers and the probe used in quantification of PRRSV is the ORF7 region. The probe was labeled with a fluorescent reporter dye, 6-carboxyfluorescein (FAM) at 5' end and a quencher dye, Black Hole Quencher 1 (BHQ_1) at 3' end. The quantification of PRRSV was performed using real-time RT-PCR on a Rotor-Gene RG-300 (Corbett Research, Sydney, AU). The 20 µl reaction mixture consisted of 10 µl 2× TaqMan Universal PCR master mix buffer (Applied Biosystems, Foster City, Calif.); 0.1 µl SuperScript III reverse transcriptase (200 U/µl) (Invitrogen, Carlsbad, Calif.); 0.2 µl RNaseout (40 U/µl) (Invitrogen, Carlsbad, Calif.); 2 µl of forward primer and reverse primer with optimum concentration; 0.8 µl of TaqMan probe with optimum concentration; 2.9 µl DNase/RNase-free water and 2 µl of 10-fold dilutions of RNA standard or 2 µl of extracted total RNA from each sample. The amplification was performed at 55° C. for 45 min, 95° C. for 10 min; then for 45 cycles at 95° C. for 15 sec and 60° C. for 60 sec each. The fluorescence was read at the end of each round of amplification. All standard dilutions and unknown samples were run in duplicate. Standard curves were accepted when the coefficients of correlation ($r^2$) were >0.99. Quantification of PRRSV were achieved by comparing the threshold cycle ($C_T$) value of the input sample RNA with the $C_T$ value of different dilutions of the standard RNA.

Serology

Blood was collected upon arrival and on Trial Days 0, 17, and 28. PRRSV antibody levels were determined using a commercial EL1SA assay (HerdChek: PRRS; IDEXX Laboratories, Westbrook, Me.).

Statistical Analysis

The data were first summarized (using means, standard deviations and histograms) to assess data quality and distributional assumptions. The data were treated as continuous (including averages of scores) or as discrete (e.g.; scores), Some of the data were repeated measures for every day (temperature and respiratory score) and analyzed by first summarizing individual pig values with the maximum or average score and then analyzed as univariate data. All other repeated measures were analyzed cross-sectionally. The data were analyzed using ANOVA, Kruskal-Wallace non-parametric ANOVA or Chi-square tests depending upon data type and distribution. Statistically significant omnibus tests were followed by post-hoc pairwise tests using the Tukey HSD adjustment (continuous data) or the Bonferroni adjustment (discrete data). One exception was the day 17 ADG variables, for which the omnibus test was statistically significant but the pairwise tests adjusted tests showed no significance among groups. For that case, pairwise tests with no adjustment were reported. Lung lobe data were averaged.

Results

Production Parameters

The overall growth performance of pigs was assessed by weigh and average daily gain (ADG) (Table 2). No statistical differences were observed in the average weights of any of the pigs in any of the groups. On day 17, the average daily gain of pigs in group 4 were significantly different in group 4 compared to pigs in group 1. No other differences were observed at any time point of the trial.

Clinical Disease

Scores for clinical disease are summarized in Table 4. Clinical respiratory scores and rectal temperatures were scored as the maximum value over time for each pig and then the average of the maximum scores were analyzed. In addition, the mean average rectal temperature was analyzed. For respiratory scores, pigs in groups 1 and 2 had significantly lower scores than observed in groups 3 and 4. For maximum rectal temperatures, pigs in group 3 had significantly higher mean average rectal temperatures than all other groups. However, no differences were observed in the average rectal temperature observed with each group.

Macroscopic, Microscopic and Immunohistochemistry (IHC) Scores

The microscopic lung lesion scores are summarized in Table 5. No differences in mean macroscopic lung lesion scores were observed with any group. Pneumonia consistent with bacterial infection was observed in 40 of the pigs in the trial. This may have also impacted the severity of the PRRSV pneumonia in this trial.

Microscopically, pigs in group 1 had significantly lower lesion score at the first necropsy compared to all other groups. No differences in microscopic lesion scores were observed at the second necropsy.

Immunohistochemistry scores for tracheobronchial lymph node, tonsil and lungs (an average of 2 sections). did not show statistical differences between the groups.

Bacteriology

*Bordetella bronchiseptica* was isolated from the respiratory tract of the majority of the pigs. In addition, a number of animals were cultured to evaluate whether swine mycoplasmas were present. Of these, *Mycoplasma hyorhinis* was isolated from 7 of 23 pigs.

Real-Time PCR (RT-PCR) Assays

Results of the RT-PCR are summarized in Table 5. Differences were observed on Trial day 10, with the levels of PRRSV RNA copy numbers being significantly higher in groups 3 and 4 compared to levels in group 2. In addition, the level of PRRSV RNA in group 4 was significantly greater at the same time point compared to group 1. No other differences in PRRSV serum RNA levels were observed at any point in the trial. No PRRSV RNA was detected on trial day 0 prior to challenge.

(tylvalosin) appeared most effective at increasing average daily gain and reducing clinical disease and the level of PRRSV viremia.

Fewer effects of Tylvalosin were observed with PRRSV induced pneumonia. No differences were observed in the severity of macroscopic pneumonia of the pigs, although the PRRSV pneumonia was, fairly severe in this challenge model. Again, as with viraemia, clinical disease and average daily gain, administration of lower doses of Tylvalosin appeared more effective in controlling disease as observed by reduced microscopic lesions at the first necropsy.

This study showed that Tylvalosin in lower doses appears to reduce clinical disease and viremia associated with PRRSV infection.

TABLE 1

Experimental design of pigs infected with PRRSV and fed Aivlosin ® (tylvalosin) and non-treated controls.

| Group | Medication/ Challenge | Number of pigs necropsied - Day 10 | Number of pigs necropsied - Day 21 | Total number of pigs |
|---|---|---|---|---|
| 1 | 100 ppm/PRRSV | 8 | 8 | 16 |
| 2 | 200 ppm/PRRSV | 8 | 8 | 16 |
| 3 | 600 ppm/PRRSV | 8 | 8 | 16 |
| 4 | 0 ppm/PRRSV | 8 | 8 | 16 |
| Total | | 32 | 32 | 64 |

TABLE 2

Average daily gain (lbs) (±standard error) of pigs infected with PRRSV and fed Aivlosin ® (tylvalosin) and non-treated controls.

| | Trial Days | | | | |
|---|---|---|---|---|---|
| Group | 0 (Baseline) | 7 | 14 | 17* | 28 |
| 1 | 9.4 ± 0.3 | 1.57 ± .09 | 1.5 ± .05 | 1.59 ± .05 A | 1.42 ± .05 |
| 2 | 9.5 ± 0.5 | 1.52 ± .10 | 1.45 ± .06 | 1.59 ± .07 A, B | 1.53 ± .07 |
| 3 | 9.6 ± 0.5 | 1.83 + .16 | 1.47 ± .06 | 1.44 ± .04 A, B | 1.47 ± .06 |
| 4 | 9.1 ± 0.4 | 1.57 ± .14 | 1.37 ± .06 | 1.40 ± .05 B | 1.45 ± .05 |
| | p = .93 | p = .52 | p = .49 | p = .03 | p = .51 |

A, B = Means with different letters within a column are statistically different.
* p-value indicates the statistical difference between treatment groups within a column.

Serology

All pigs were serum antibody negative on Trial Day 0. On trial day 17, 2 pigs in groups 1 and 2 and one pig in each of groups 3 and 4 remained seronegative for PRRSV antibodies. All other pigs were seropositive. All remaining pigs were seropositive by the end of the trial.

Discussion

PRRSV remains a significant problem to the swine industry. ECO Animal Health was interested in assessing the ability of Aivlosin® (tylvalosin)) to reduce clinical disease and viremia associated with PRRSV infection. Differences were observed in average daily gain on trial day 17 and in the severity of clinical disease as measured by respiratory scoring and the maximum rectal temperature. In addition, the level of PRRSV RNA was different between groups at trial day 10 which was 3 days following inoculation of PRRSV. No other differences in levels were observed, however there was a wide variation in levels of RNA measured in each individual group making interpretation of the data difficult. Interestingly, the lower doses of Aivlosin®

TABLE 3

Summation of clinical disease of pigs infected with PRRSV and fed Aivlosin ® (tylvalosin) and non-treated controls.

| Group | Mean maximum respiratory score | Mean maximum rectal temperature* | Mean average rectal temperature |
|---|---|---|---|
| 1 | 0.5 ± 0.1 A* | 104.5 ± 0.2 A | 103.6 ± 0.1 |
| 2 | 0.6 ± 0.2 A | 104.7 ± 0.2 A | 103.7 ± 0.1 |
| 3 | 1.8 ± 0.3 B | 105.8 ± 0.3 B | 103.8 ± 0.1 |
| 4 | 1.6 ± 0.3 B | 104.9 ± 0.2 A | 103.7 ± 0.1 |
| | P < .0001 | p = .004 | p = .43 |

A, B = Means with different letters within a column are statistically different.
* p-value indicates the statistical difference between treatment groups within a column.

TABLE 4

Mean microscopic PRRSV lung lesion scores (±standard error) of pigs infected with PRRSV and fed Aivlosin ® (tylvalosin) and non-treated controls.

| Group | Microscopic lesions | |
|---|---|---|
| | Necropsy 1* | Necropsy 2 |
| 1 | 0.2 ± 0.2 A | 2.1 ± 0.4 |
| 2 | 2.0 ± 0.3 B | 1.9 ± 0.3 |
| 3 | 2.0 ± 0.3 B | 1.5 ± 0.3 |
| 4 | 3.1 ± 0.2 B | 1.6 ± 0.2 |
| | p = .0034 | p = .49 |

A, B = Means with different letters within a column are statistically different.
* p-value indicates the statistical difference between treatment groups within a column.

TABLE 5

Mean real-time reverse transcriptase polymerase chain reaction assay (RT-PCR) (±standard error in ( )) of pigs infected with PRRSV and fed Tylvalosin and non-treated controls.

| Group | 0 | 10* | 17 | 21 | 28 |
|---|---|---|---|---|---|
| 1 | ND* | 15,289.88 B, C (10,376.85) | 95,315.72 (39,810.62) | 36,451.13 (18,412.13) | 5,301.63 (4,255.46) |
| 2 | ND | 19,336.8 C (14,608.2) | 78,804.81 (13,955.73) | 18,724.88 (8,119.57) | 892.36 (205.60) |
| 3 | ND | 54,487.19 A, B (21,036.27) | 146,655.4 (39,291.16) | 30,260.69 (12,238.41) | 1,292.31 (384.53) |
| 4 | ND | 88,993.13 A (62,389.83) | 94,018.09 (31,455.92) | 23,983.88 (7,888.66) | 2,817.63 (1,777.98) |
| | | p = .0016 | p = .49 | p = .84 | p = .96 |

*ND = not detectable
A, B = Means with different letters within a column are statistically different.
* p-value indicates the statistical difference between treatment groups within a column.

REFERENCES

Antohe F, Serban G, Radulescu L, Simionescu M. (1997). Transcytosis of albumin in endothelial cells is brefeldin A-independent. *Endothelium*, 5:125-36.

Bosnar, M, Kelneric, Z., Munic, V., Erakovic, V. and Parnham, M. J. (2005) Cellular uptake and efflux of azithromycin, erythromycin, clarithromycin, telithromycin and cethromycin. *Antimicrobial Agents and Chemotherapy*, 49: 2372-2377.

Carbon C. (1995). Clinical relevance of intracellular and extracellular concentrations of macrolides. *Infection*, 23: S10-14.

Chu J J, Ng M L. (2002). Infection of polarized epithelial cells with flavivirus West Nile: polarized entry and egress of virus occur through the apical surface. *Journal of General Virology*, 83:2427-35.

Chin A C Morck D W Merrill J K Ceri H Olon M E Read R R Dick P Buret A G (1998) Anti-inflammatory benefits of tilmicosin in calves with *Pasteurella haemolytica*-infected lungs. *American Journal of Veterinary Research*, 59: 765-771

Cordo S M, Cesio y Acuna M, Candurra N A. (2005). Polarized entry and release of Junin virus, a New World arenavirus. *Journal of General Virology*, 86:1475-9.

Ellinger I, Rothe A, Grill M, Fuchs R. (2001). Apical to basolateral transcytosis and apical recycling of immunoglobulin G in trophoblast-derived BeWo cells: effects of low temperature, nocodazole, and cytochalasin D. *Experimental Cell Research*, 269: 322-31.

Gladue R. P and Snider M. E. 1990. Intracellular accumulation of azithromycin by cultured human fibroblasts. *Antimicrob Agents Chemother.* 34(6):1056-60.

Ianaro A Ialenti A mafia P Sautebin L Rombola L Carnuccio R Iuvone T D'Acquisto F DiRosa M (2000). Anti-inflammatory activity of macrolide antibiotics. *Journal of Pharmacology and Experimental Therapeutics*, 292:156-163.

Halbur P G, Paul P S, Frey M L, et al. Comparison of the pathogenicity of the two U S porcine reproductive and respiratory syndrome virus isolates with that of the Lelystad virus. *Vet Pathol* 1995; 32: 648-660.

Halber P G, Miller L D, Paul P S, et al. Immunohistochemical identification of porcine reproductive and respiratory system virus (PRRSV) antigen in the heart and lymphoid system of three-week-old colostrum-deprived pigs. *Vet Pathol* 1995; 32:200-204.

Jarvis M A, Wang C E, Meyers H L, Smith P P, Corless C L, Henderson G J, Vieira J, Britt W J, Nelson J A. (1999). Human cytomegalovirus infection of caco-2 cells occurs at the basolateral membrane and is differentiation state dependent. *Journal of Virology*, 73:4552-60.

Kaiserlian D, Rigal D, Abello J, Revillard J P. (1991). Expression, function and regulation of the intercellular adhesion molecule-1 (ICAM-1) on human intestinal epithelial cell lines. *European Journal of Immunology*, 21: 2415-21.

Labro M-T (1993). Effects of macrolides on host natural defenses. In; Macrolides chemistry, pharmacology and clinical use. pp 389-408. Ed. Brysker A, Paris; Arnette-Blackwell.

Labro M-T (1996). Intracellular bioactivity of macrolides. *Clinical Microbiology and Infection*, 1: S24-30.

Labro, M-T. (2000). *Interference of antibacterial agents with phagocyte functions: immunomodulation or "immuno fairy tales"?* Clinical Microbiology Reviews, 13: 615-650.

Maples C J, Ruiz W G, Apodaca G. (1997). Both microtubules and actin filaments are required for efficient postendocytotic traffic of the polymeric immunoglobulin receptor in polarized Madin-Darby canine kidney cells. *The Journal of Biological Chemistry*, 272:6741-51.

Mengeling W L, Lager K M, Vorwald A C. Diagnosis of porcine reproductive and respiratory syndrome. *J Vet Diagn Invest* 1995; 7:3-16.

Molmenti, E P Ziambaras T Perlmutter, D H (1993). Evidence for an acute phase response in human intestinal epithelial cells. *The Journal of Biological Chemistry*, 268:14116-14124.

Nightingale C H (1997). Pharmacokinetics and pharmacodynamics of newer macrolides. *Pediatric Infectious Disease Journal*, 16:438-443.

Okamoto R, Tsuchiya M, Nomura H, Iguchi H, Kiyoshima K, Hori S, Inui T, Sawa T Takeuchi T Umezawa H (1981). Biological properties of new acyl derivatives of tylosin. *The Journal of Antibiotics*, 33: 1309-1315.

Pelkmans L, Helenius A (2003). Insider information: what viruses tell us about endocytosis. *Current opinion in cell biology*, 15:414-22.

Reeve-Johnson, L Kempf I. Gesbert F. Guittet M (1997a). Efficacy of tilmicosin in the control of experimental *Mycoplasma gallisepticum* infection in chickens. *Journal of veterinary pharmacology and therapeutics,* 20: 148-149.

Reeve-Johnson, L Kempf I. Charleston B (1997b). An evaluation of the efficacy of tilmicosin treatment and control measure against artificial infection with *Mycoplasma gallisepticum* in chickens *Journal of veterinary pharmacology and therapeutics* 20: 132.

Rossen J W, Kouame J, Goedheer A J, Vennema H, Rottier P J. (2001). Feline and canine coronaviruses are released from the basolateral side of polarized epithelial LLC-PK1 cells expressing the recombinant feline aminopeptidase-N cDNA. *Archives of Virology,* 146:791-9.

Scorneaux B, Shryock T R. (1998a). Intracellular accumulation, subcellular distribution and efflux of tilmicosin in swine phagocytes. *Journal of veterinary pharmacology and therapeutics,* 21:257-68.

Scorneaux B, Shryock T R. (1998b). Intracellular accumulation, subcellular distribution, and efflux of tilmicosin in chicken phagocytes. *Poultry Science* 77:1510-21.

Scorneaux B, Shryock T R. (1999). The determination of the cellular volume of avian, porcine and bovine phagocytes and bovine mammary epithelial cells and its relationship to uptake of tilmicosin. *Journal of veterinary pharmacology and therapeutics* 22:6-12.

Sood R, Bear C, Auerbach W, Reyes E, Jensen T, Kartner N, Riordan J R, Buchwald M. (1992). Regulation of CFTR expression and function during differentiation of intestinal epithelial cells. *The EMBO Journal* 11: 2487-94.

Stuart L M, Ezekowitz R A. (2005). Phagocytosis: elegant complexity. *Immunity.* 22:539-50.

Sunazuka, T., Yoshida, K., Oohori, M., Haragaya, Y., Iwai, Y., Akagawa, K. S. and Omura, S. (2003) Effects of 14-membered macrolide compounds on monocyte to macrophage differentiation. *The Journal of Antibiotics.* 56: 721-724.

Tsuchiya M, Suzukake K, Hon M Sawa T Takeuchi T Umezawa H. (1981) Studies on the effects of 3-acetyl-4"-isovaleryltylosin against multiple-drug resistant strains of *Staphylococcus aureus. The Journal of Antibiotics* 34: 305-312.

Tulkens P M (1991). Intracellular distribution and activity of antibiotics. *European journal of clinical microbiology and infectious diseases* 10:100-106.

Varilek G W, Neil G A, Bishop W P. (1994). Caco-2 cells express type I interleukin-1 receptors: ligand binding enhances proliferation. *The American journal of physiology* 267: G1101-7.

Zweibaum A, Triadou N, Kedinger M, Augeron C, Robine-Leon S, Pinto M, Rousset M, Haffen K. (1983) Sucrase-isomaltase: a marker of foetal and malignant epithelial cells of the human colon. *International journal of cancer,* 15:407-12.

TABLE 6

| Family | Genus | Virus | Example host |
| --- | --- | --- | --- |
| Adenoviridae | Mastadenovirus | adenovirus 7 | Man |
| Arteriviridae | Arterivirus | porcine respiratory and reproductive syndrome | Pig |
| Asfarviridae | Asfarvirus | African swine fever virus | Pig |
| Bunyaviridae | Hantavirus | Puumala virus | Man |
| Circoviridae | Circovirus | porcine circovirus 2 | Pig |
| Coronaviridae | Coronavirus | infectious bronchitis virus | Fowl |
| | | transmissible gastroenteritis virus (TGEV) | Pig |
| | | SARS CoV | Man |
| Filoviridae | Marburgvirus | Marburg Lake Victoria | Man |
| Filoviridae | Ebolavirus | Reston, Sudan, Ivory coast, Zaire Ebolavirus | Man |
| Flaviviridae | Flavivirus | West Nile virus | Man, horse, birds |
| | | yellow fever virus | Man |
| | | tick borne encephalitis virus | Man |
| Flaviviridae | Pestivirus | bovine virus diarrhoea virus | Cattle |
| | | classical swine fever | Pig |
| Flaviviridae | Hepacivirus | hepatitis C | Man |
| | | | Man, fowl, pig, horse |
| Orthomyxoviridae | Influenzavirus A | influenza A virus, influenza B virus | Dog |
| Orthomyxoviridae | Isavirus | salmon infectious anaemia virus | Salmon |
| Parvoviridae | Parvovirus | canine parvovirus | Dog |
| Picornaviridae | Entero | Coxsackie B3, B5 | Man |
| Picornaviridae | Rhino | major subgroup | Man |
| Picornaviridae | Rhino | minor subgroup | Man |
| Reoviridae | Orthoreovirus | avian reovirus | Fowl |
| Reoviridae | Rotavirus | rotavirus | Man, sheep, pig, cattle |
| Togaviridae | Alphavirus | Semliki forest virus | Man |
| | | hepatitis E virus | pig |

The invention claimed is:

1. A method of treating a virus infection comprising administering tylvalosin or an ester or salt thereof, to a subject having a viral infection, wherein the virus is influenza.

2. The method according to claim 1, wherein the virus is Influenza virus A.

3. The method according to claim 1, wherein the administering of tylvalosin or an ester or salt thereof, is also for preventing or treating a bacterial infection.

4. The method according to claim 3, wherein the bacterial infection is an infection with one or more of *Mycoplasma* hyopneumoniae, Actinobacillus pleuropneumoniae, Pasteurella multocida, Streptococcus suis and Bordetella brochiseptica.

5. The method according to claim 3, wherein the bacterial infection is an infection with one or more of Staphylococcus aureus, Streptococci haemolyticus, Pneumococci, Pseudomanoas aeruginosa, and Haemophilus influenzae.

6. The method according to claim 3, wherein the bacterial infection is an infection with Mycoplasma zallisep

UNITED STATES PATENT AND TRADEMARK OFFICE
CERTIFICATE OF CORRECTION

PATENT NO. : 9,649,324 B2
APPLICATION NO. : 14/733801
DATED : May 16, 2017
INVENTOR(S) : Albert Philip Adrian Mockett et al.

Page 1 of 1

It is certified that error appears in the above-identified patent and that said Letters Patent is hereby corrected as shown below:

On the Title Page

Item (62), Related U.S. Application Data should read:
(62) Division of application No. 12/373,657, filed as application No. PCT/GB2007/002620 on Jul. 13, 2007, now Pat. No. 9,066,964.

Signed and Sealed this
Thirteenth Day of November, 2018

Andrei Iancu
*Director of the United States Patent and Trademark Office*